(12) United States Patent
Chang et al.

(10) Patent No.: US 11,998,619 B2
(45) Date of Patent: Jun. 4, 2024

(54) COMPOUND, ANTIINFLAMMATORY DRUG COMPRISING THE COMPOUND AND CYCLOOXYGENASE-2 INHIBITOR COMPRISING THE COMPOUND

(71) Applicant: Yong Min Chang, Daegu (KR)

(72) Inventors: Yong Min Chang, Daegu (KR); Hee Kyeong Kim, Daegu (KR); Seungtae Woo, Daegu (KR); Seonguk Jin, Daegu (KR); Sung Bo Kyung, Daegu (KR)

(73) Assignee: Yong Min Chang, Daegu (KR)

( * ) Notice: Subject to any disclaimer, the term of this patent is extended or adjusted under 35 U.S.C. 154(b) by 28 days.

(21) Appl. No.: 16/982,856

(22) PCT Filed: Mar. 22, 2019

(86) PCT No.: PCT/KR2019/003353
§ 371 (c)(1),
(2) Date: Sep. 21, 2020

(87) PCT Pub. No.: WO2019/182395
PCT Pub. Date: Sep. 26, 2019

(65) Prior Publication Data
US 2021/0052748 A1    Feb. 25, 2021

(30) Foreign Application Priority Data

Mar. 22, 2018 (KR) .................. 10-2018-0033426
Mar. 12, 2019 (KR) .................. 10-2019-0027841

(51) Int. Cl.
| A61K 49/10 | (2006.01) |
| A61K 33/244 | (2019.01) |
| A61P 29/00 | (2006.01) |
| C07D 257/02 | (2006.01) |

(52) U.S. Cl.
CPC .......... *A61K 49/108* (2013.01); *A61K 33/244* (2019.01); *A61P 29/00* (2018.01); *C07D 257/02* (2013.01)

(58) Field of Classification Search
CPC .. A61K 33/244; A61K 47/547; A61K 49/108; A61K 49/10; A61P 29/00; A61P 9/10; A61P 25/00
See application file for complete search history.

(56) References Cited

U.S. PATENT DOCUMENTS

| 2005/0002859 A1 | 1/2005 | Marnett et al. |
| 2010/0111858 A1 | 5/2010 | Howard et al. |
| 2011/0092806 A1* | 4/2011 | Port ..................... A61K 49/085 |
| | | 424/1.65 |
| 2015/0086616 A1* | 3/2015 | Lehrer ................. A61K 9/1694 |
| | | 514/567 |

FOREIGN PATENT DOCUMENTS

KR            102068727         1/2020

OTHER PUBLICATIONS

De Vries et al., Current Pharmaceutical Design, 2006, 12, p. 3847-3856. (Year: 2006).*
International Search Report and Written Opinion Issued in Corresponding PCT Patent Application PCT/KR2019/003353, dated Jul. 4, 2019.
Sung, "Gadolinium-Complexes of D03A Conjugates as Inflammation Targeted Magnetic Resonance Imaging Contrast Agents," Thesis for the Degree of Master of Science, Department of Medical & Biological Engineering The Graduate School Kyungpook National University. Feb. 2018, inner pp. 1-37.
Kim, et al., "Gd3+Based MRI Contrast Agents as Potential Inflammation Targeting," The 5th International Conference on MRI (ICMR12017) and 22nd Annual Scientific Meeting of KSMRM. Mar. 23-25, 2017, P106.
Uddin, et al., "Design, Synthesis, and Structure-Activity Relationship Studies of Fluorescent Inhibitors of Cycloxygenase-2 as Targeted Optical Imaging Agents," *Bioconjugate Chemistry*, 24: 712-723, 2013.

* cited by examiner

*Primary Examiner* — Michael G. Hartley
*Assistant Examiner* — Leah H Schlientz
(74) *Attorney, Agent, or Firm* — NORTON ROSE FULBRIGHT US LLP

(57) ABSTRACT

A compound is disclosed that can be used as an anti-inflammatory agent, a cyclooxygenase-2 inhibitor, a therapeutic agent for brain diseases, or a MRI contrast medium. The compound can have the structure represented by chemical formula 1.

6 Claims, 11 Drawing Sheets

[FIG. 1]
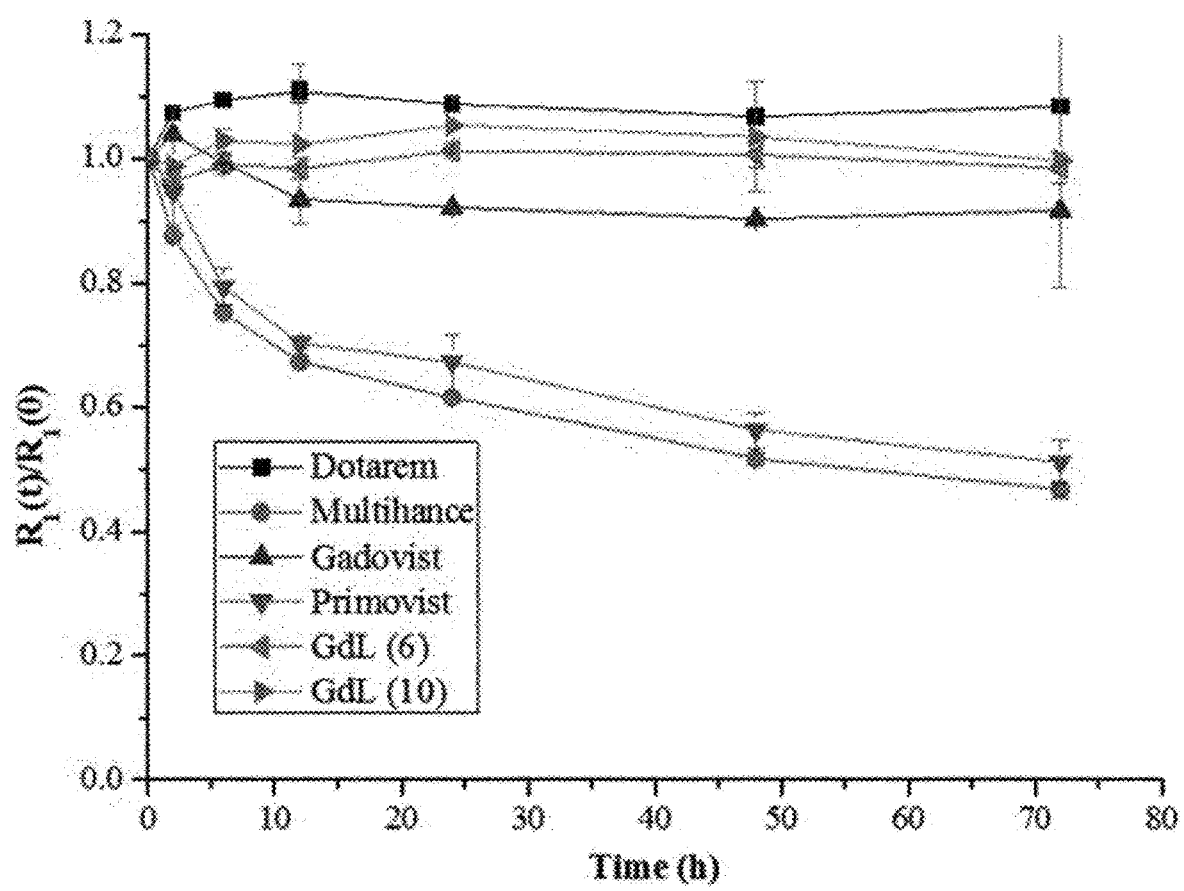

[FIG. 2A]
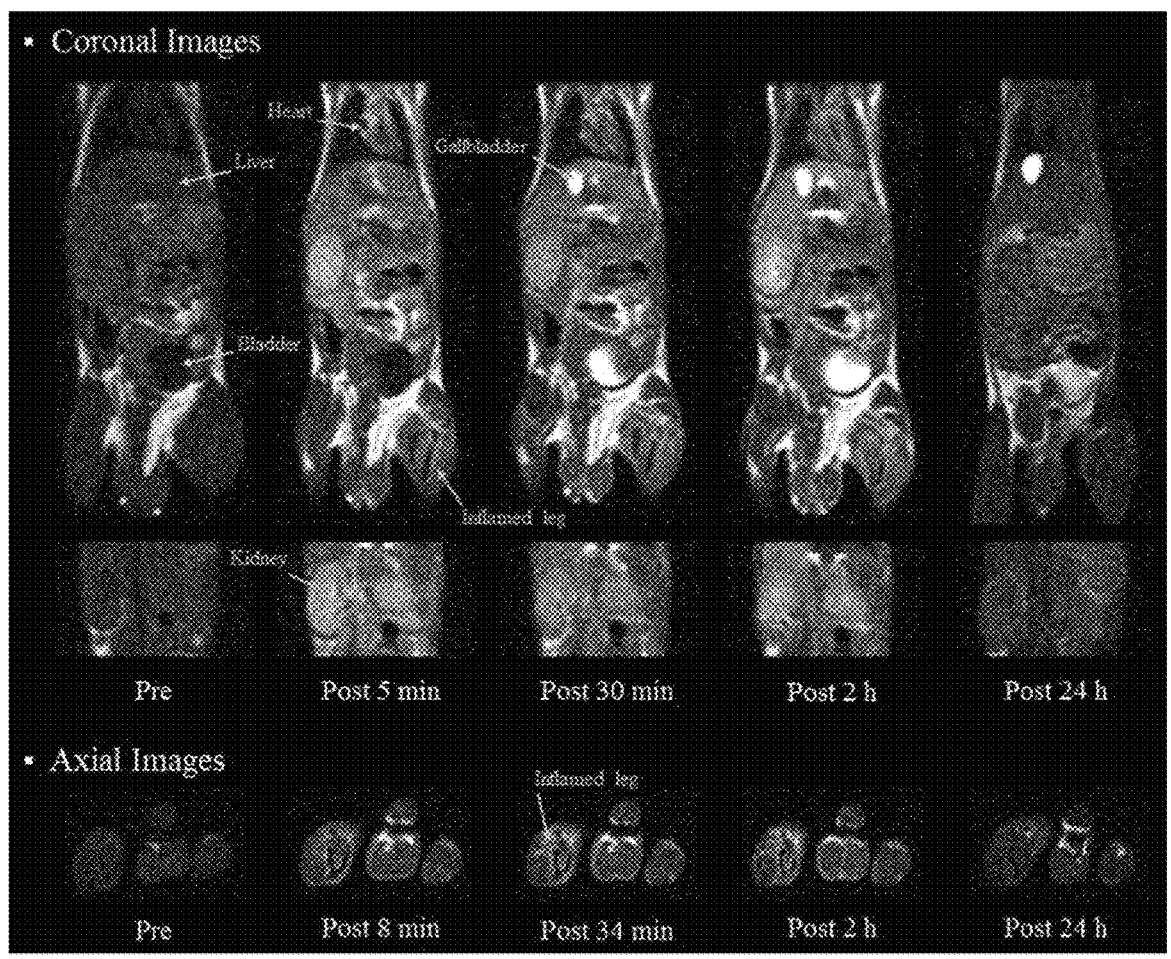

[FIG. 2B]
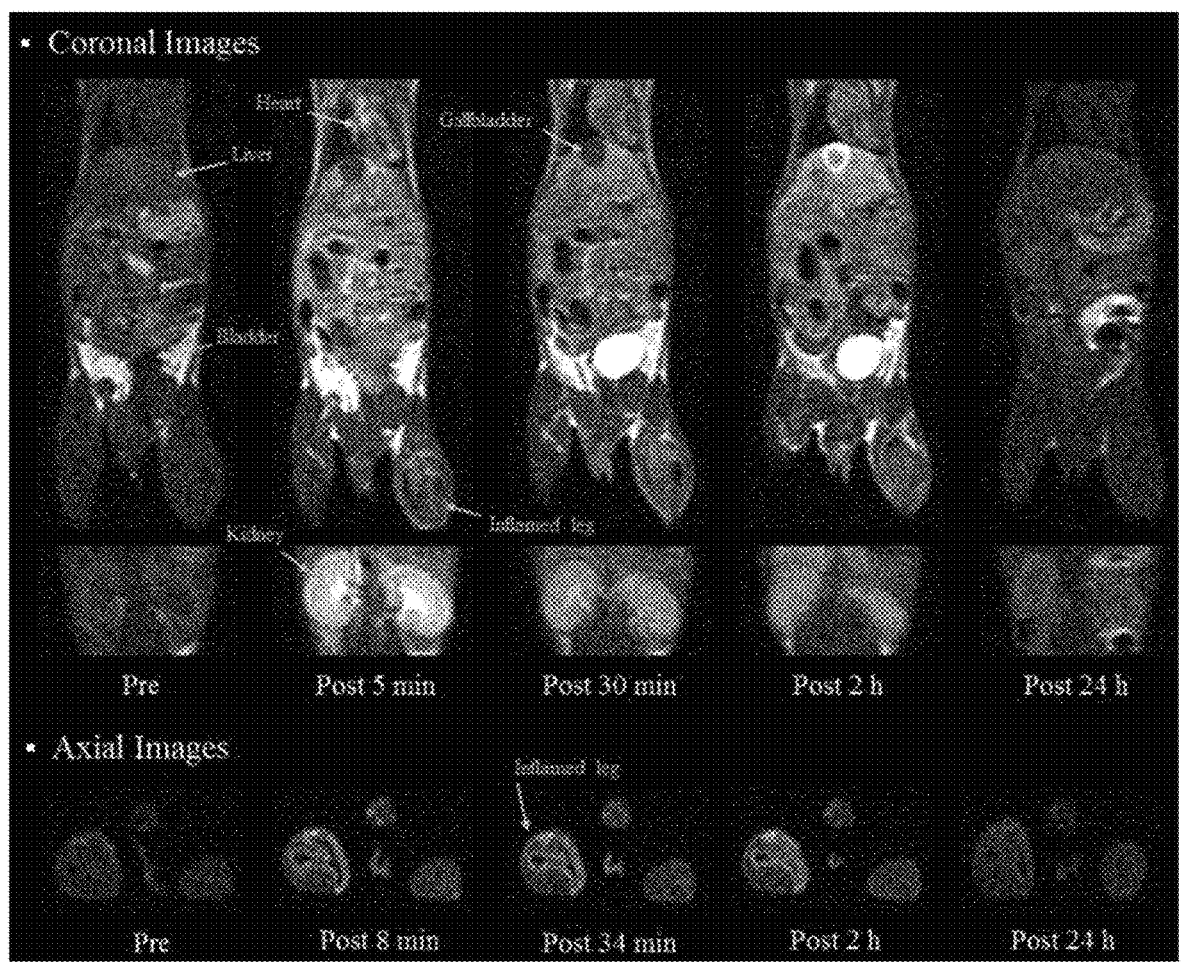

[FIG. 2C]
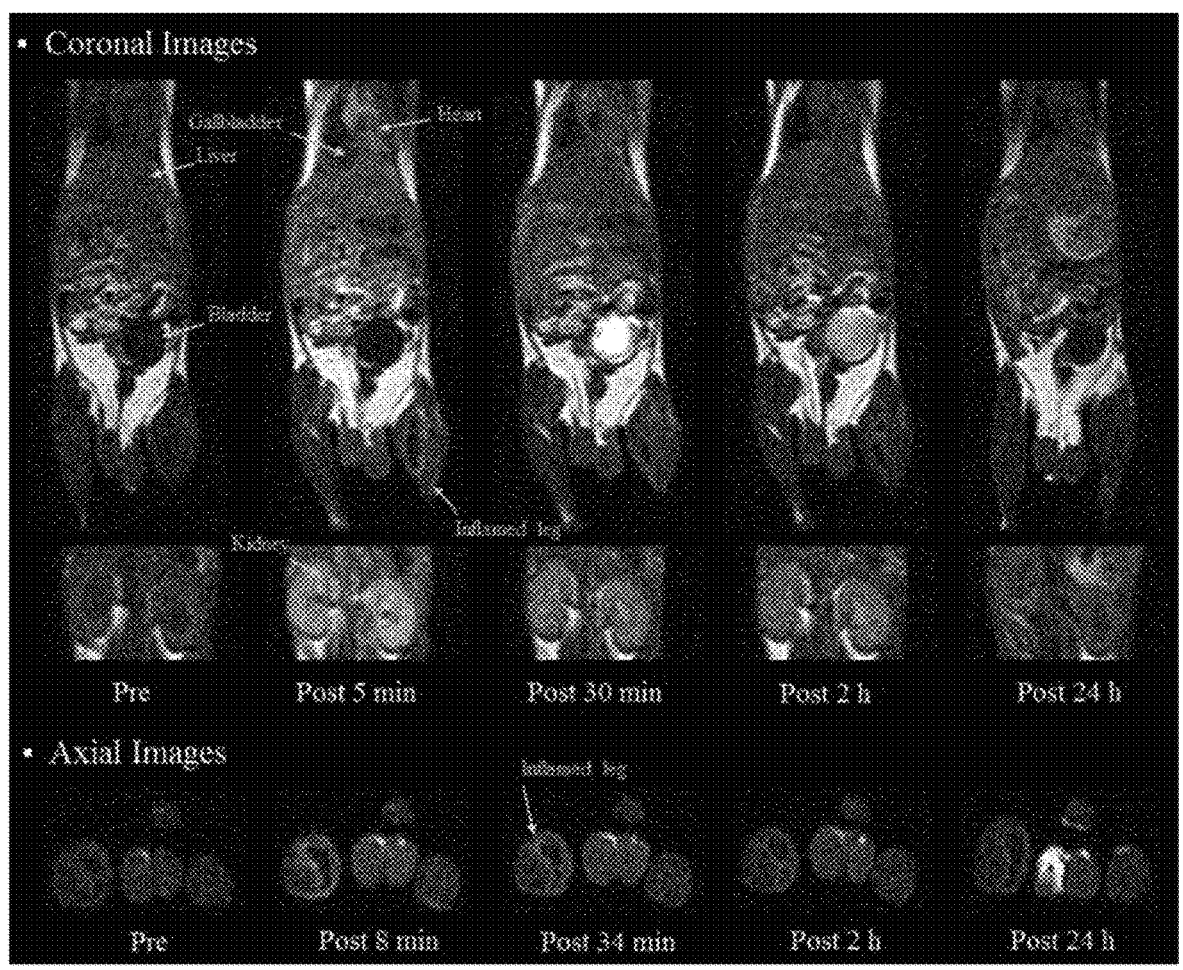

【FIG. 2D】
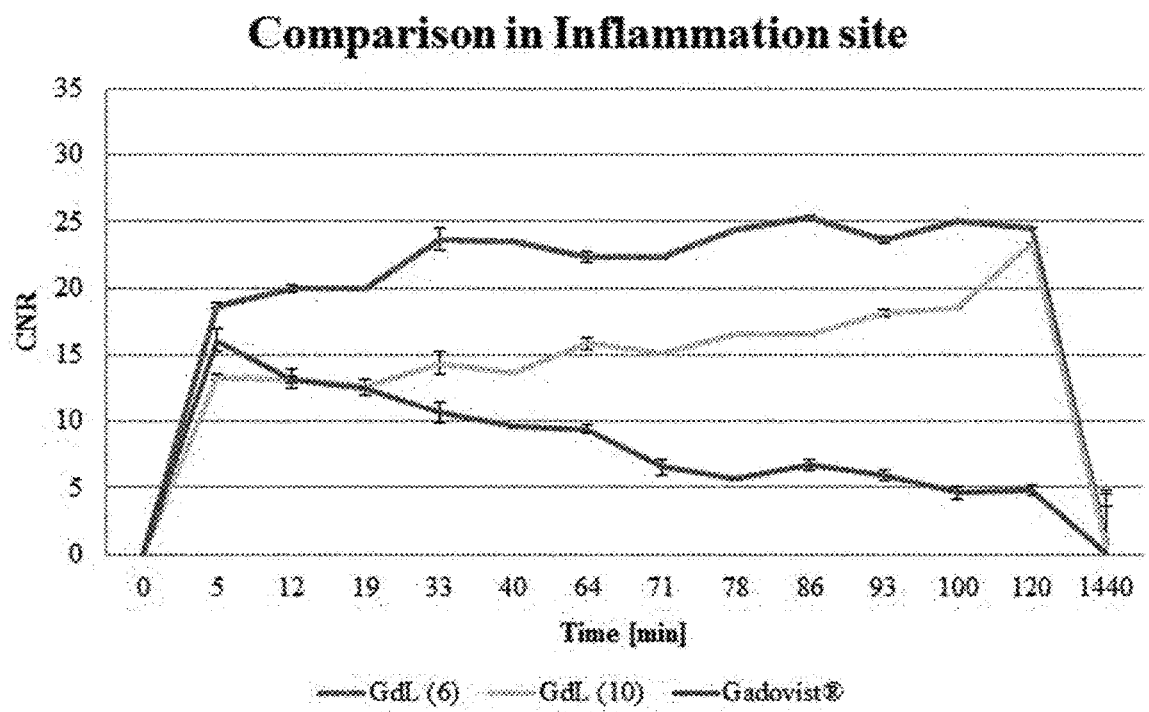
【FIG. 3】
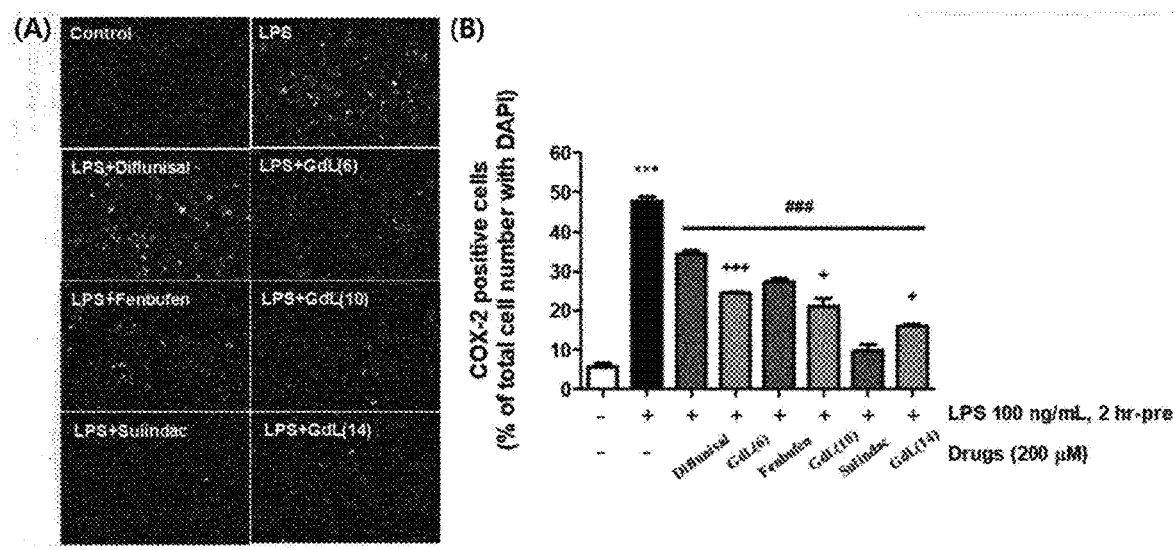

[FIG. 4]
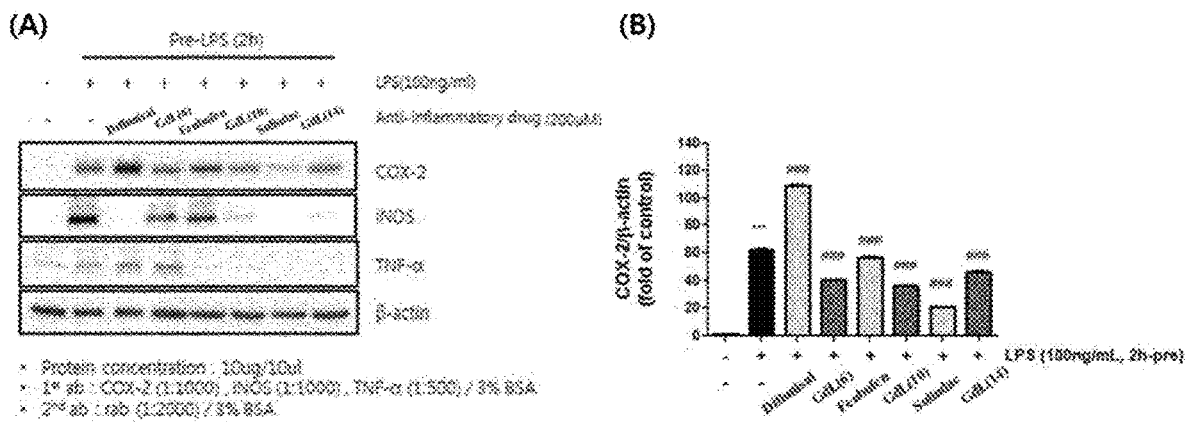
[FIG. 5A]
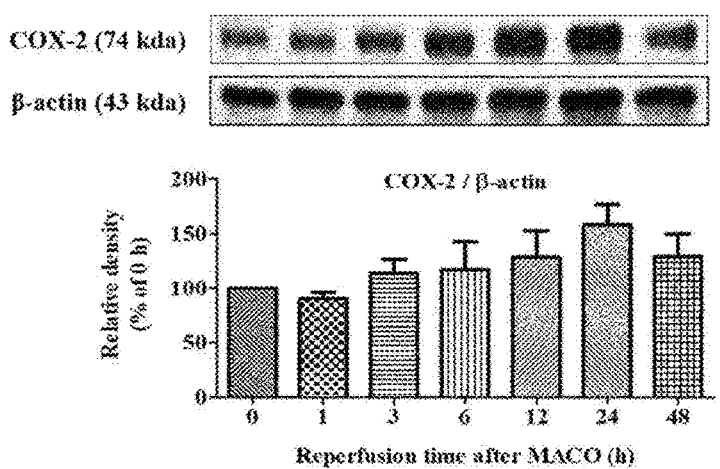

[FIG. 5B]
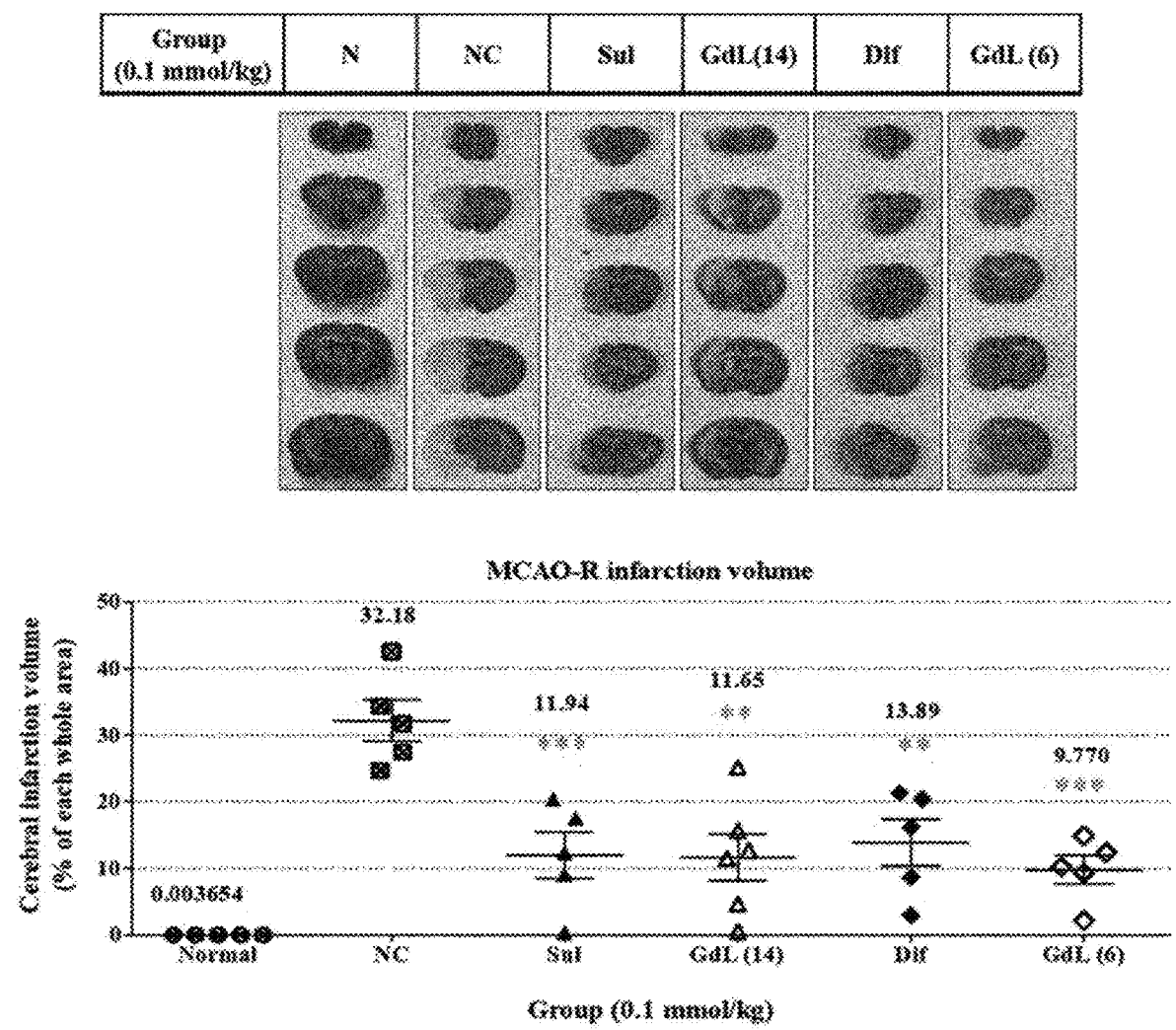

[FIG. 5C]
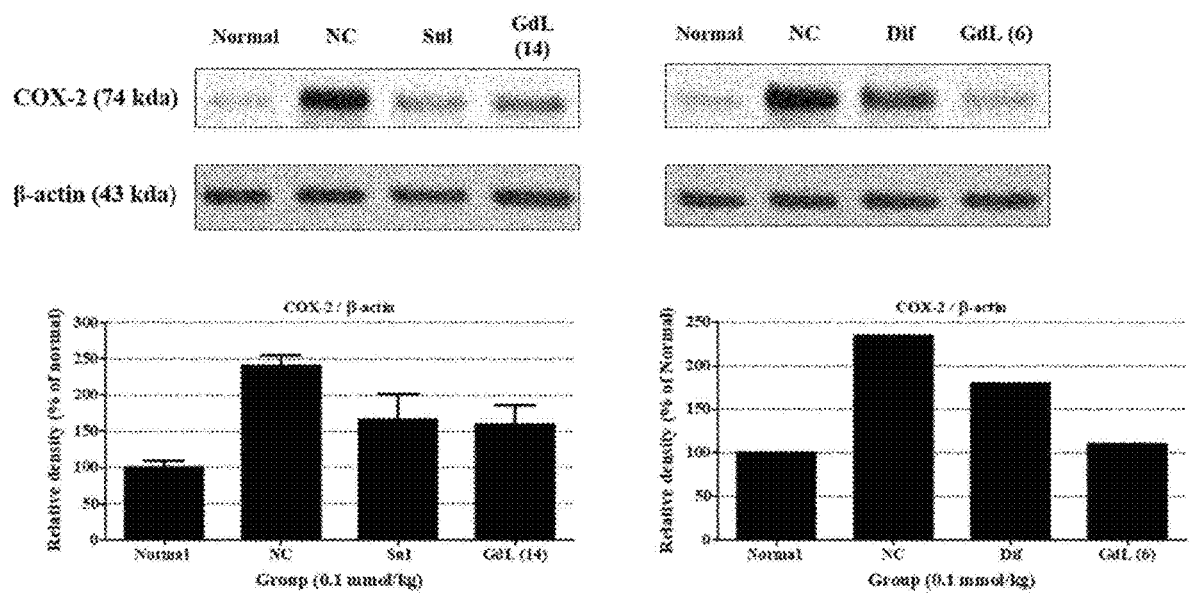

[FIG. 6]
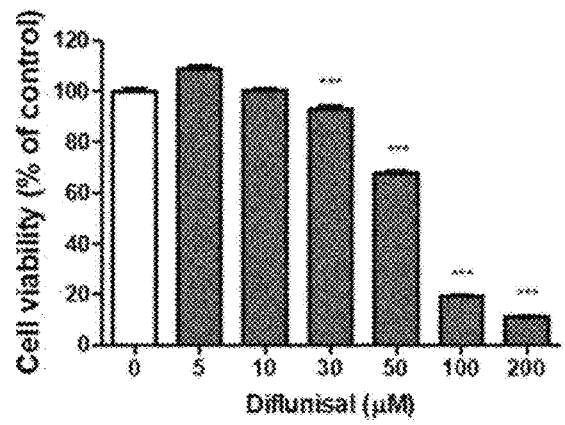
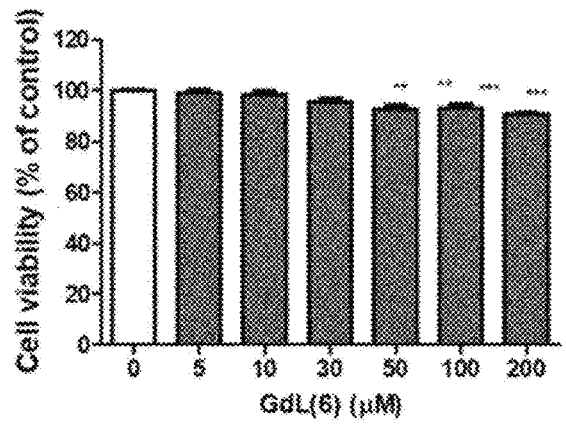
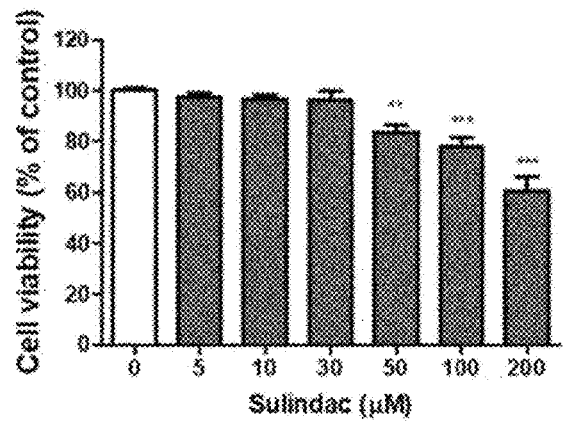
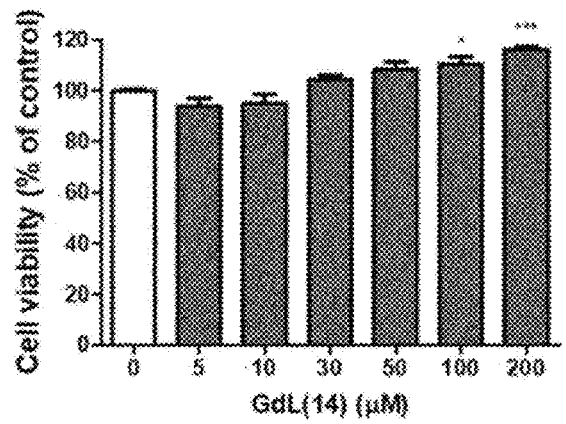

[FIG. 7]
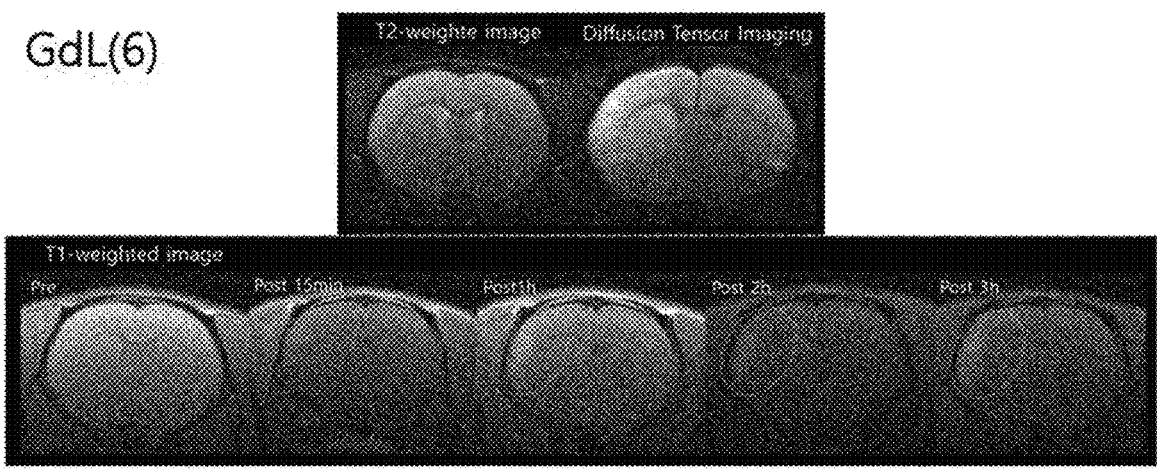
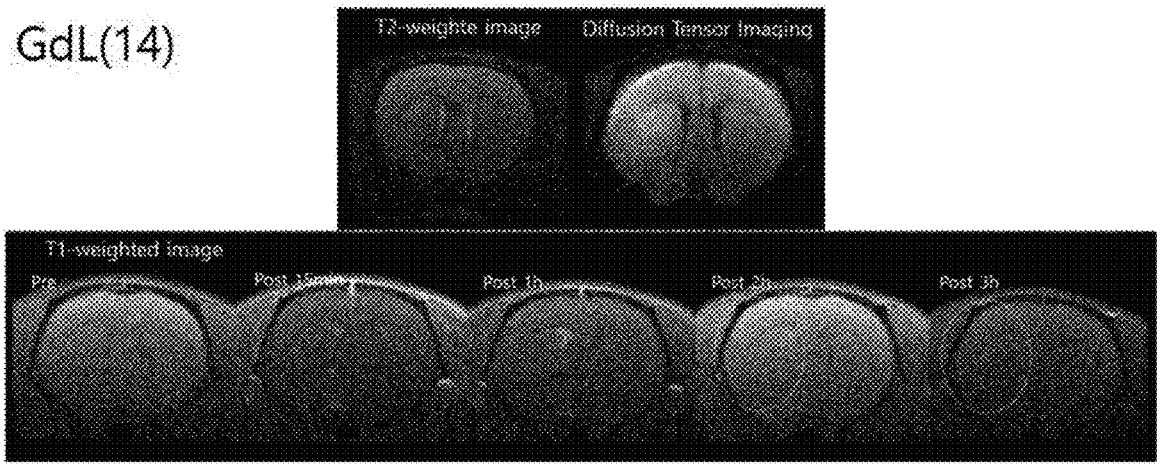

[FIG. 8]
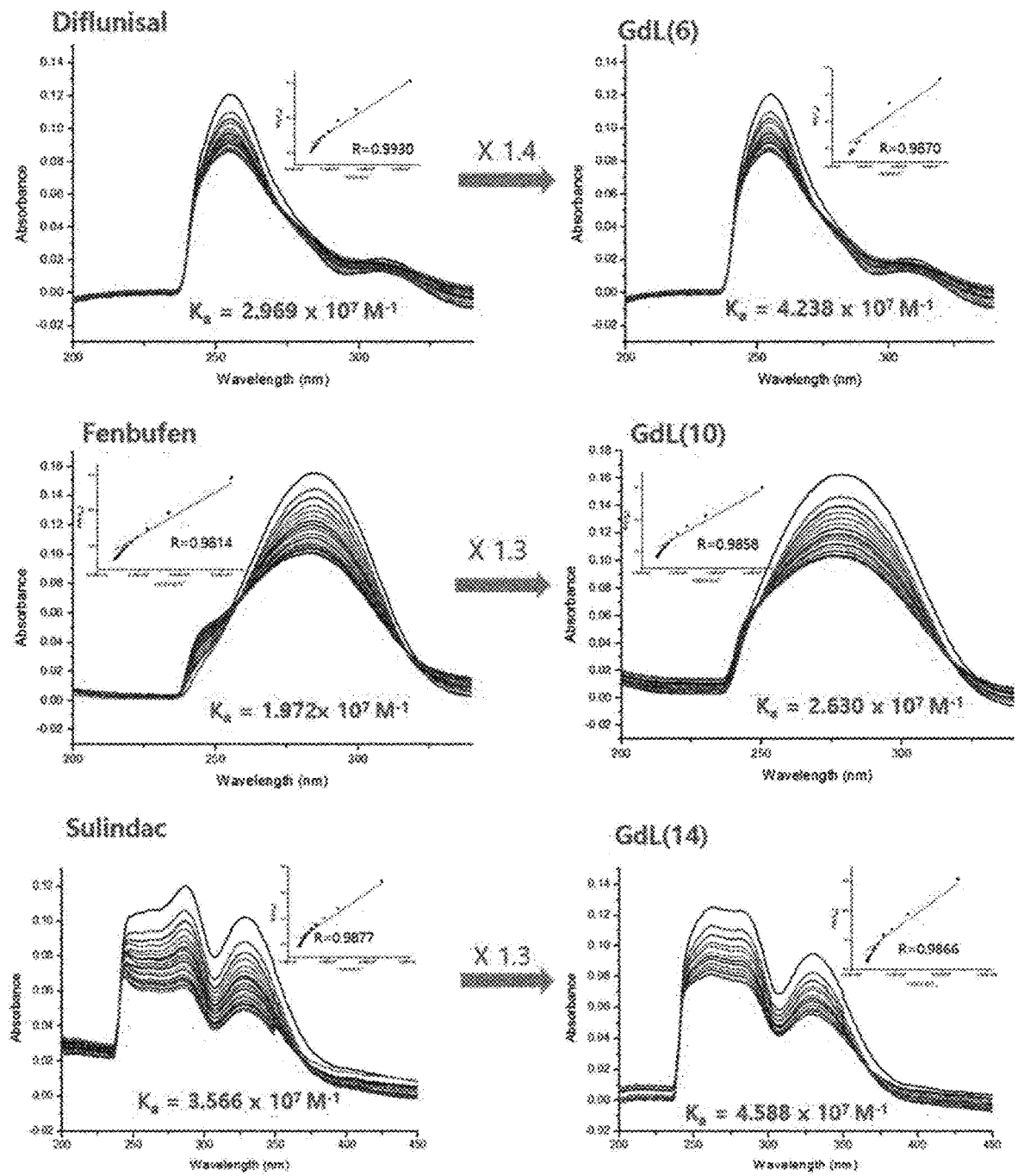

COMPOUND, ANTIINFLAMMATORY DRUG COMPRISING THE COMPOUND AND CYCLOOXYGENASE-2 INHIBITOR COMPRISING THE COMPOUND

CROSS REFERENCE TO RELATED APPLICATIONS

This application is a national phase under 35 U.S.C. § 371 of International Application No. PCT/KR2019/003353, filed Mar. 22, 2019, which claims the benefit of priority to Korean Patent Application Serial No. 10-2018-0033426, filed Mar. 22, 2018, and Korean Patent Application Serial No. 10-2019-0027841, filed Mar. 12, 2019, the entire contents of each of which are hereby incorporated by reference in their entirety.

FIELD OF THE INVENTION

The present disclosure relates to a compound with a novel structure. More specifically, the present disclosure relates to a compound having a novel structure having high relaxivity and capable of targeting and treating an inflammation site and thus capable of simultaneously targeting, diagnosing and treating the inflammation site, an anti-inflammatory agent containing the compound, and cyclooxygenase-2 inhibitors containing the compound.

DESCRIPTION OF RELATED ART

An inflammatory mediator is a factor that plays an important pathogenic role in initiation, transmission and persistence of pain and inflammation. Prostagalandin is a major inflammatory mediator.

Nonsteroidal anti-inflammatory drugs (NSAIDs) block cyclooxygenase (COX) which is mainly involved in biosynthesis of prostagalandin, and thus are used in acute and chronic diseases with pain and inflammation. In general, NSAIDs block cyclooxygenase-1 (COX-1) and cyclooxygenase-2 (COX-2) among cyclooxygenases, thereby inhibiting the synthesis of prostagalandin of arachidonic acid, thereby reducing pain and inflammation.

However, while COX-2 is rarely expressed in normal times and is rapidly induced locally via inflammatory reaction caused by harmful stimuli, and is involved in the inflammatory reaction, COX-1 is expressed in most of tissues and is involved in maintaining normal cellular functions, and thus is responsible for maintaining homeostasis such as protection of gastrointestinal mucosa, blood vessel homeostasis, platelet aggregation, and renal function maintenance. Thus, inhibition of COX-1 may cause side effects such as gastrointestinal bleeding, cardiovascular serum reaction, myocardial infarction, and stroke occurring in a stomach and a cardiovascular system.

Therefore, in order to avoid such as the abnormal reaction, an anti-inflammatory substance that may selectively inhibit only COX-2 which is expressed via the inflammatory reaction and sustains and worsens the inflammatory reaction is required. However, most of conventional NSAIDs inhibit both COX-1 and COX-2. Thus, research and development of a new anti-inflammatory substance exhibiting selective inhibition properties of COX-2 are further required.

SUMMARY OF THE INVENTION

One purpose of the present disclosure is to provide a compound with a novel structure.

Another purpose of the present disclosure is to provide an anti-inflammatory agent containing the compound.

Another purpose of the present disclosure is to provide a cyclooxygenase-2 (COX-2) inhibitor containing the compound.

One aspect of the present disclosure provides a compound having a structure represented by a following Chemical Formula 1:

[Chemical Formula 1]

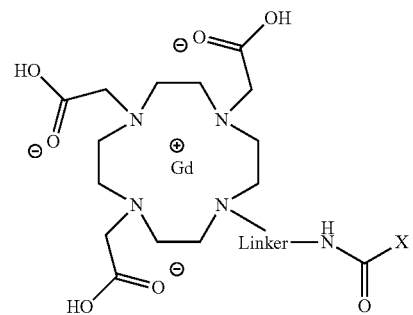

wherein in the Chemical Formula 1, the linker represents *—$(CH_2)_x$-A-$(CH_2)_y$—*, wherein each of x and y independently represents an integer from 0 to 5, wherein A represents *—COO—*, *—CO—*, *—CONH—* or *—O—*, wherein X represents:

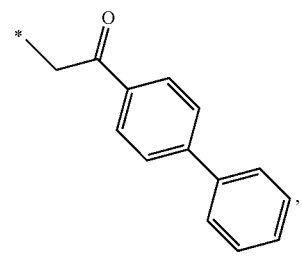

,

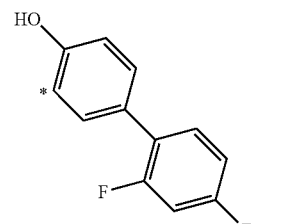

, or

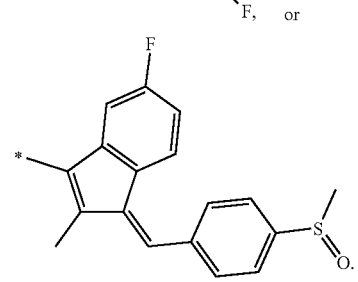

The Chemical Formula 1 is represented by a following Chemical Formula 2, 3, or 4:

[Chemical Formula 2]

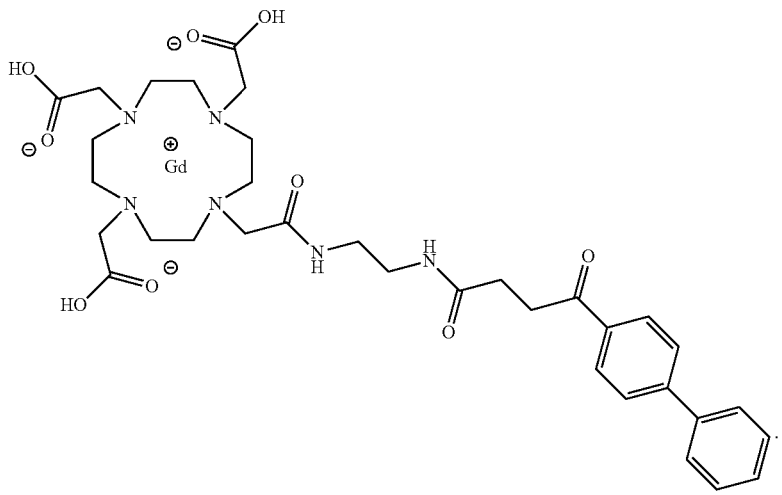

[Chemical Formula 3]

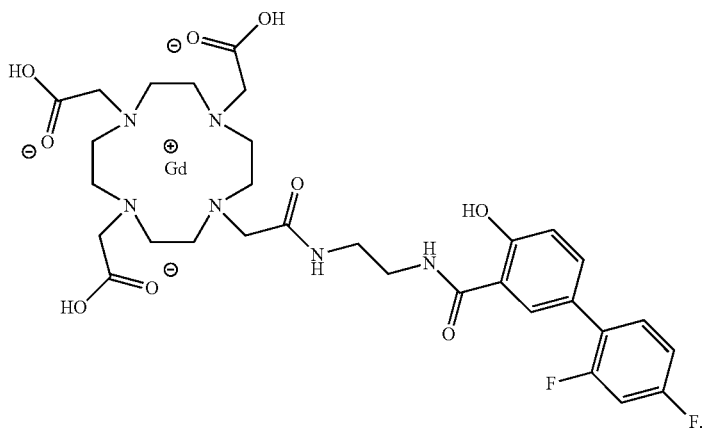

[Chemical Formula 4]

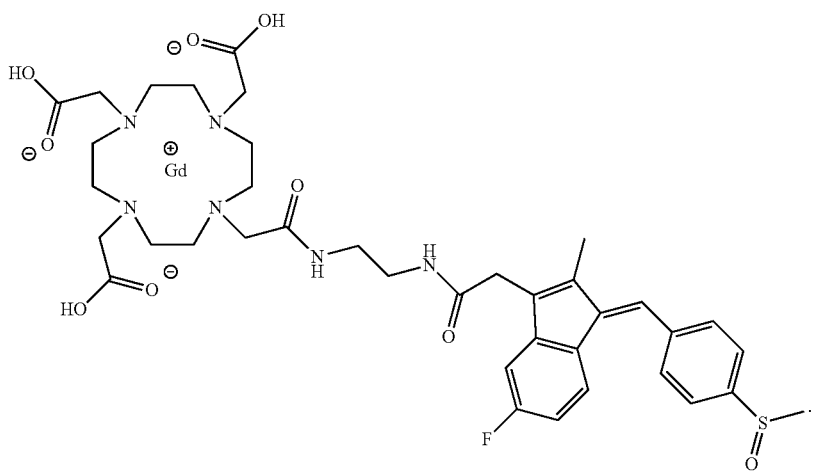

The compound targets an inflammation site and diagnoses the inflammation site in a targeting manner, and has anti-inflammatory activity on the inflammation site.

Particularly, the compound of each of the Chemical Formulas 1 to 3 has anti-inflammatory activity by selectively inhibiting cyclooxygenase-2 (COX-2) at an inflammation site.

The compound of each of the Chemical Formulas 3 and 4 is used for targeting diagnosis of a brain inflammation site, and has anti-inflammatory activity on the brain inflammation site.

The compound has relaxivity of 4 $mM^{-1}s^{-1}$ to 5 $mM^{-1}s^{-1}$ on a 1.5 T magnetic resonance image (MRI).

The compound coordinates with at least one water molecule.

Another aspect of the present disclosure provides an anti-inflammatory agent containing a compound having a structure represented by the Chemical Formula 1, wherein the anti-inflammatory agent targets an inflammation site and has anti-inflammatory activity on the inflammation site.

The Chemical Formula 1 is represented by each of the above Chemical Formulas 2 to 4. The anti-inflammatory agent selectively inhibits cyclooxygenase-2 (COX-2) at an inflammation site. The anti-inflammatory agent selectively inhibits only cyclooxygenase-2 (COX-2) among cyclooxygenase-1 (COX-1) and cyclooxygenase-2 (COX-2) at an inflammation site.

The compound of each of the Chemical Formulas 3 and 4 targets a brain inflammation site, and has anti-inflammatory activity on the brain inflammation site.

Still another aspect of the present disclosure provides a MRI contrast agent containing a compound having a structure represented by the above Chemical Formula 1, wherein the MRI contrast agent has relaxivity of 4 mM$^{-1}$s$^{-1}$ to 5 mM$^{-1}$s$^{-1}$ on a 1.5 T magnetic resonance image (MRI).

The Chemical Formula 1 is represented by each of the above Chemical Formulas 2 to 4.

Particularly, the MRI contrast agent containing the compound of each of the Chemical Formulas 3 and 4 specifically targets a cerebral infarction site to strongly increase a signal related to the cerebral infarction site.

Still yet another aspect of the present disclosure provides a cyclooxygenase-2 inhibitor containing a compound having a structure represented by the above Chemical Formula 1. The Chemical Formula 1 is represented by each of the above Chemical Formulas 2 to 4.

Still yet another aspect of the present disclosure provides a therapeutic agent for treating a brain inflammatory disease, the therapeutic agent contains a compound having a structure represented by a following Chemical Formula 1:

[Chemical Formula 1]

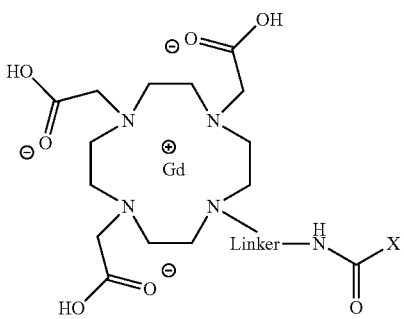

wherein in the Chemical Formula 1, the linker represents *—(CH$_2$)$_x$-A-(CH$_2$)$_y$—*, wherein each of x and y independently represents an integer from 0 to 5, wherein A represents *—COO—*, *—CO—*, *—CONH—* or *—O—*, wherein X represents:

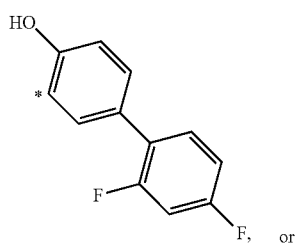

, or

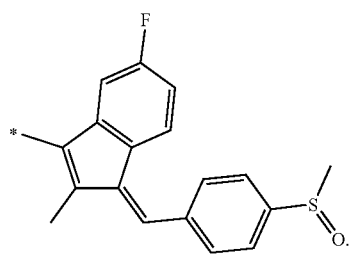

.

The brain inflammatory disease may include dementia. The dementia may include cerebrovascular dementia or degenerative dementia. The COX-2 is a factor that expresses as an inflammatory factor in a high level regardless of whether the dementia is the cerebrovascular or degenerative dementia, thereby to exacerbate the disease condition.

The Chemical Formula 1 is represented by a following Chemical Formula 3 or 4:

[Chemical Formula 3]

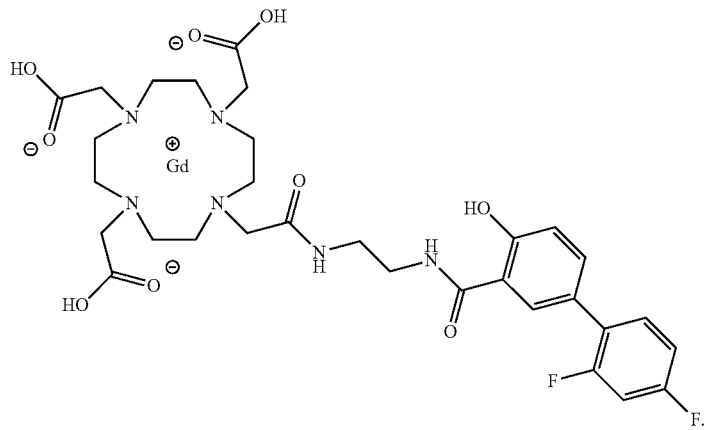

-continued

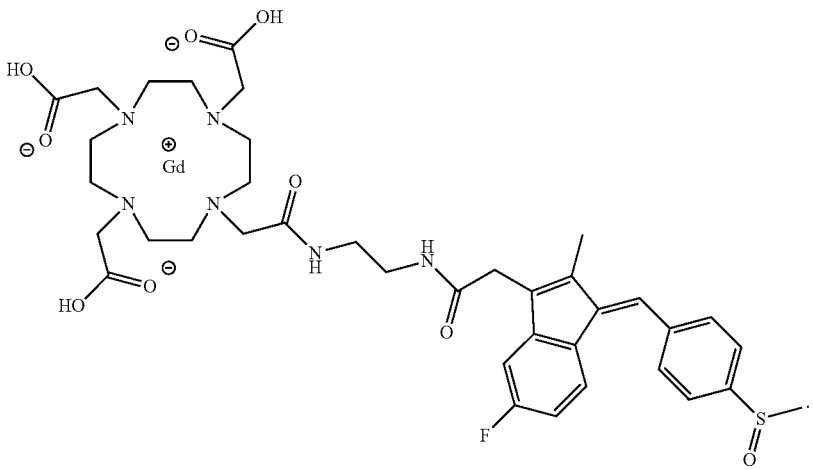

[Chemical Formula 4]

The compound according to the present disclosure, the anti-inflammatory agent containing the same and the cyclooxygenase-2 inhibitor containing the same targets the inflammation site, has anti-inflammatory activity on the inflammation site, and, at the same time, has relaxivity properties, thereby diagnosing the inflammation site in a targeting manner. The compound according to the present disclosure exhibits relaxivity higher than that of a conventional commercially-available MRI contrast agent, and has excellent kinematic stability. In particular, the compound according to the present disclosure may enhance a signal intensity related to the inflammation site for a longer period than the conventional contrast agent does and thus may be used as a contrast agent having excellent property capable of diagnosis of the inflammation site in a targeting manner. Further, the compound according to the present disclosure may selectively inhibit the cyclooxygenase-2 activity at the inflammation site, and thus may be used as the cyclooxygenase-2 selective inhibitor. In addition, the compound may exhibit effective anti-inflammatory activity via the inhibition of the cyclooxygenase-2, and thus may be used as an anti-inflammatory agent having excellent anti-inflammatory activity. Therefore, the compound according to the present disclosure may be used as an anti-inflammatory agent and the COX-2 selective inhibitor capable of diagnosis the inflammation site of inflammatory diseases including rheumatoid arthritis in a targeting manner and at the same time capable of treating the inflammatory disease.

BRIEF DESCRIPTION OF THE DRAWINGS

FIG. 1 is a diagram to describe kinematic stability of a compound according to the present disclosure.

FIG. 2A and FIG. 2B are diagrams to describe an evaluation result of inflammation targeting ability of a compound according to the present disclosure.

FIG. 2C is a diagram to describe an evaluation result of inflammation targeting ability of a commercially-available contrast agent Gadovist®.

FIG. 2D is a CNR graph to describe an evaluation result of inflammation targeting ability of each of a compound according to the present disclosure and a commercially-available contrast agent Gadovist®.

FIG. 3 is a diagram to describe anti-inflammatory properties of a compound according to the present disclosure.

FIG. 4 is a diagram to describe COX-2 selective inhibition property of a compound according to the present disclosure.

FIG. 5A shows a result of an animal experiment on acute cerebral stroke or vascular dementia among brain inflammatory diseases. FIG. 5B shows an experimental result of cerebral infarction caused by ischemic stroke. FIG. 5C shows identification via a western blot technique of a protein amount of COX-2 as an inflammatory factor as expressed at a tissue of a cerebral infarction site as caused by ischemic stroke.

FIG. 6 shows a result of a cell viability experiment of brain cerebral cortex microglia in GdL(6) and GdL(14) according to the present disclosure, and in diflunisal and sulindac as conventional substances.

FIG. 7 shows a result that in both of GdL(6) and GdL(14) enhance an ischemia site related signal in a stroke animal model.

FIG. 8 shows a COX-2 target affinity result of each of GdL(6), GdL(10), and GdL(14) as three substances according to the present disclosure, and each of diflunisal, fenbufen, and sulindac as comparative substances.

DETAILED DESCRIPTIONS

Hereinafter, an embodiment of the present disclosure will be described in detail with reference to the accompanying drawings. The present disclosure may have various changes and various forms in terms of implementations thereof. Specific embodiments will be illustrated in the drawings and will be described in detail herein. However, it should be understood that the specific embodiments are not intended to limit the present disclosure thereto, and rather the present disclosure includes all of changes, equivalents, or substitutes included in the spirit and scope of the present disclosure. In describing the drawings, similar reference numerals have been used for similar elements.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A compound according to the present disclosure has a structure represented by a following Chemical Formula 1:

[Chemical Formula 1]

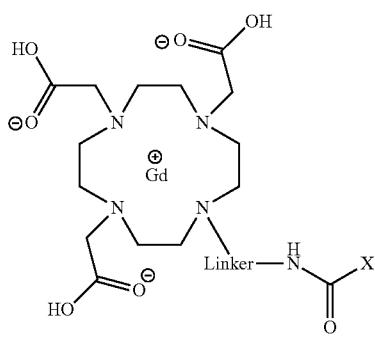

wherein in the Chemical Formula 1, the linker represents *—(CH$_2$)$_x$-A-(CH$_2$)$_y$—*, wherein each of x and y independently represents an integer from 0 to 5, wherein A represents *—COO—*, *—CO—*, *—CONH—* or *—O—*, wherein X represents:

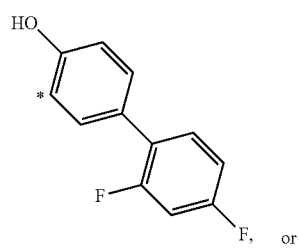

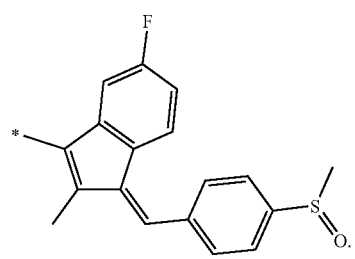

In this connection, * means a binding site.

In the compound according to the present disclosure represented by the Chemical Formula 1, gadolinium (Gd) may coordinate with at least one water molecule. In this connection, in the compound, gadolinium may form a coordination bond with an oxygen atom of the linker A.

In one example, the compound according to the present disclosure represented by the Chemical Formula 1 may be a compound represented by a following Chemical Formula 2:

[Chemical Formula 2]

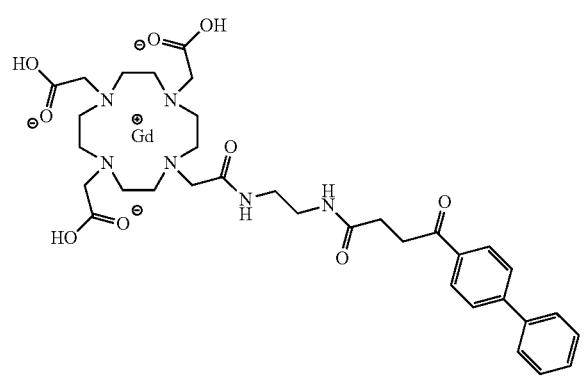

Alternatively, the compound according to the present disclosure represented by the Chemical Formula 1 may be a compound represented by a following Chemical Formula 3:

[Chemical Formula 3]

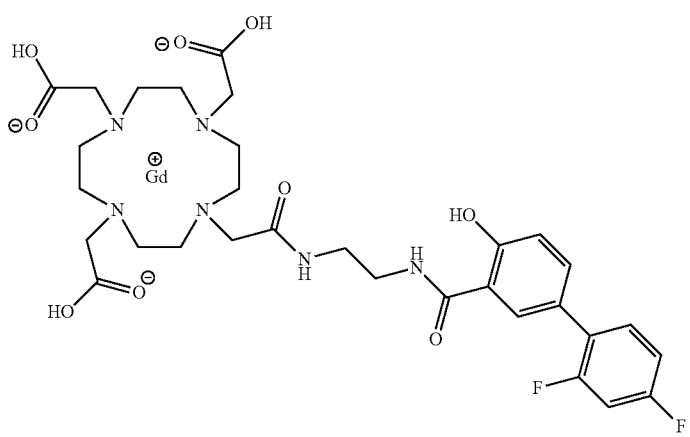

The compounds according to the present disclosure has targetability toward an inflammation site and may exhibit anti-inflammatory effect on the inflammation site. Specifically, the compound according to the present disclosure may target the inflammation site and suppress expression of cyclooxygenase (COX) induced at the inflammation site. Accordingly, the compound may prevent synthesis of prostagalandin of arachidonic acid induced from COX, thereby to exhibit anti-inflammatory activity that blocks initiation, propagation, and persistence of an inflammatory response. In this connection, the compound according to the present disclosure has selective inhibition property of cyclooxygenase-2 (COX-2) at the inflammation site, thereby to prevent side effects such as gastrointestinal bleeding, perforation, or cardiovascular disease which a majority of conventional nonsteroidal anti-inflammatory drugs (NSAIDs) that inhibit both of cyclooxygenase-1 (COX-1) and cyclooxygenase-2 (COX-2) have. Therefore, the compound according to the present disclosure may be used as a COX-2 selective inhibitor or an anti-inflammatory agent.

Further, the compound according to the present disclosure has excellent relaxivity property. The relaxivity property refers to property capable of exhibiting contrast enhancement on a magnetic resonance image (MRI). The magnetic resonance imaging refers to a method of obtaining an image of anatomy, physiological, and biochemical information of a body using phenomenon of relaxation of a spin of a hydrogen atom in a magnetic field. When obtaining the MRI, an external substance is injected to the body to increase an image contrast. The substance is referred to as a contrast agent. A relaxation action in which a nuclear spin of a water molecule in the tissue returns to an equilibrium state varies based on the tissues. Thus, a contrast between images of the tissues occurs. The contrast agent may affect the relaxation action to increase a difference between relaxations of the tissues to cause change in a MRI signal, and thus play a role in allowing the contrast between the images of the tissues to be clearer. The contrast agent needs to have high thermodynamic stability, water solubility, and to bind to at least one water molecule and thus have high relaxivity properties with water. The compound according to the present disclosure is capable of having the coordination bond with at least one water molecule and has relaxivity properties. Thus, the compound may bind to at least one water molecule in the body to increase the relaxation of hydrogen atoms in the water molecule to improve the image contrast. Therefore, the compound according to the present disclosure may be used as a contrast agent for MRI. In this connection, the compound according to the present disclosure may be a positive contrast agent that relatively increases an image signal of a target body site on MRI. The compound according to the present disclosure may exhibit excellent relaxivity of 4 $mM^{-1}s^{-1}$ to 5 $mM^{-1}s^{-1}$, for example, on a 1.5 T magnetic resonance image.

In addition, as described above, the compound according to the present disclosure may target the inflammation site. Thus, the compound according to the present disclosure may be used as a contrast agent that targets an inflammation site of an inflammatory disease such as rheumatoid arthritis and allows diagnosis thereof in a targeting manner. Further, the compound according to the present disclosure may exhibit anti-inflammatory activity by selectively inhibiting COX-2 at the inflammation site, and thus may diagnose and treat the inflammation site at the same time. In other words, the compound according to the present disclosure may be a compound capable of targeting and diagnosing the inflammation site and, at the same time, of treating the inflammation site via the anti-inflammatory activity on the inflammation site. Accordingly, a multifunctional anti-inflammatory agent and COX-2 inhibitor containing the compound according to the present disclosure and thus capable of simultaneously targeting and diagnosing and treating the inflammation site may be realized.

Hereinafter, the compound according to the present disclosure, a preparation method thereof, and an anti-inflammatory agent and a COX-2 inhibitor, each containing the compound according to the present disclosure will be described based on Examples.

Synthesis of Compound According to the Present Disclosure (1) Synthesis of Ligand To prepare the compound according to the present disclosure, first, a ligand having a cyclic structure was synthesized. Specifically, tri-tert-butyl2,2',2"-(1,4,7,10-tetraazacyclododecane-1,4,7-triyl)triacetate) (5 g, 9.72 mmol) was dissolved in 160 mL of acetonitrile (ACN), and then potassium hydrogen carbonate ($KHCO_3$) (2.96 g, 29.69 mmol) was added thereto, followed by stirring for 30 minutes. Then, ethyl bromoacetate (1.18 mL, 10.69 mmol) was added thereto, and heating thereof to 60° C. was conducted and thus reaction thereof has occurred for 24 hours. Then, an insoluble reactant was filtered away therefrom and the solvent of the reactant was completely removed therefrom. Then, a reaction product was dissolved in dichloromethane (DCM), and an insoluble reactant was filtered away therefrom, and the solvent of the reactant was removed therefrom, and the reaction product was dried in vacuum. Thus, tri-tert-butyl2,2',2"-(10-(2-ethoxy-2-oxoethyl)-1,4,7,10-tetraazacyclododecane-1,4,7-triyl)triacetate) (hereinafter, compound (1)) as a slightly yellowish colored solid was obtained (yield: 5.8 g (99%)).

Subsequently, the compound (1) (3.2 g. 5.33 mmol) was dissolved in 7 mL methanol (MeOH), and then 6 mL of ethylenediamine was added thereto, followed by reaction at room temperature for 4 days. Then, a container receiving a reaction product was connected to a vacuum line, and was heated to about 55° C., and the solvent was removed therefrom to obtain an oily state solid. The solid was washed several times with diethyl ether, was dried under vacuum, and then was dissolved in MeOH. Then, the insoluble reactant was filtered away therefrom, and the resulting solution was subjected to open column chromatography under a DCM/MeOH condition, thereby to obtain tri-tert-buty2,2',2"-(10-(2-((2-aminoethyl)amino)-2-oxoethyl)-1,4,7,10-tetraazacyclododecane-1,4,7-triyl)triacetate (DO3A$^t$(Bu)$_3$-NH$_2$) (hereinafter, compound (2)) as a slightly yellowish colored solid (yield: 1.87 g (57%)).

A synthesis reaction of the compounds (1) and (2) may be expressed as a following Reaction Formula 1:

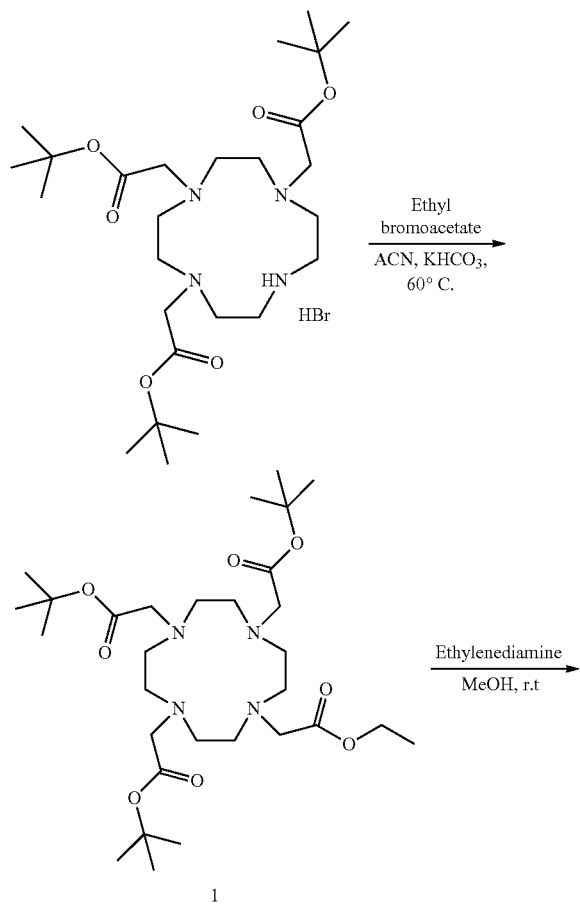

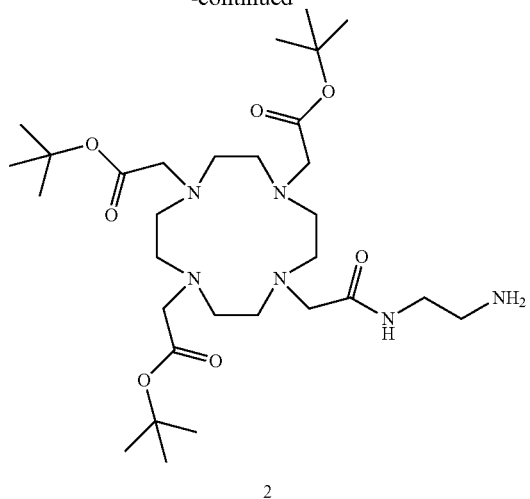

In the Reaction Formula 1, 1 represents the compound (1) and 2 represents the compound (2).

(2) Synthesis of GdL (6) as Compound According to Example 1 of the Present Disclosure First, diflunisal (3 g, 12 mmol) was dissolved in 40 mL tetrahydrofuran (THF), and then N-hydroxysuccinimide (NHS) was added thereto, followed by stirring for 30 minutes. Then, N,N'-dicyclohexylcarbodiimide (DCC) dissolved in 30 mL THF was slowly added thereto at 4° C. and then reaction thereof has occurred at room temperature for 24 hours. Then, an insoluble reactant was filtered therefrom, and the solvent was completely removed therefrom, and then, a resulting product was subjected to open column chromatography (DCM/MeOH, 99:1), thereby to separate and purify 2,5-dioxopyrrolidin-1-yl 2',4'-difluoro-4-hydroxy-[1,1'-biphenyl]-3-carboxylate) (hereinafter, compound (3)) as a white colored solid (yield: 2.36 g (57%)).

Then, the compound (3) (2.36 g, 6.8 mmol) dissolved in 20 mL THF and the compound (2) (3.5 g, 5.7 mmol) dissolved in 20 mL MeOH were mixed with each other and reacted with each other at room temperature for 24 hours. Then, the solvent was completely removed therefrom, ands extraction thereof was performed under a DCM/deionized water condition. A DCM layer was dehydrated with sodium sulfate (Na$_2$SO$_4$) and the solvent was removed therefrom. Thereafter, a resulting product was subjected to open column chromatography (DCM/MeOH, 98:2), thereby to separate and purify tri-tert-butyl2,2',2"-(10-(2-((2-(2',4'-difluoro-4-hydroxy-[1,1'-biphenyl]-3-carboxamido)ethyl)amino)-2-oxoethyl)-1,4,7,10-tetraazacyclododecane-1,4,7-triyl)triacetate) (hereinafter, compound (4)) as a white solid (yield: 2.7 g (56%)).

Then, the compound (4) (2.5 g, 2.95 mmol) was dissolved in DCM/TFA (1:1, 40 mL) at 0° C., and reaction thereof has occurred at room temperature for 24 hours. The solvent of the reactant was removed therefrom and a resulting product was dissolved in 10 mL of MeOH, and was precipitated in 200 mL of diethyl ether. The precipitate was filtered and was subjected to prep. HPLC, thereby to separate 2,2',2"-(10-(2-((2-(2',4'-difluoro-4-hydroxy-[1,1'-biphenyl]-3-carboxamido)ethyl)amino)-2-oxoethyl)-1,4,7,10-tetraazacyclododecane-1,4,7-triyl)triacetic acid) (hereinafter, compound (5)) as a white solid. In this connection, a yield was 1.91 g (95%).

Subsequently, the compound (5) (0.25 g, 0.368 mmol) was dissolved in DI water, and pH of the solution was adjusted to 3 using 1 M NaOH to form a first solution. Then, gadolinium chloride hexahydrate (GdCl$_3$.6H$_2$O) (0.15 g, 0.405 mmol) was dissolved in 1 mL of water to form a solution. The solution was gradually added to the first solution. pH of the reaction product was adjusted to 7 using 1 M NaOH and reaction has occurred at 55° C. for 18 hours. Then, the solvent was removed therefrom. Then, the reaction product was subjected to prep. HPLC, thereby to separate and purify a compound according to Example 1 of the present disclosure (hereinafter, GdL (6)) as a white solid (yield: 0.21 g (68%)).

A synthesis reaction of the compound according to Example 1 of the present disclosure may be expressed as a following Reaction Formula 2:

(3) Synthesis of GdL (10) as Compound According to Example 2 of the Present Disclosure Further, in order to prepare the compound according to Example 2 of the present disclosure, first, fenbufen (2.5 g, 9.83 mmol) was dissolved in 40 mL of THF, and then NHS was added thereto, followed by stirring thereof for 30 minutes. Then, DCC dissolved in 30 mL of THF was slowly added thereto at 4° C. and then reaction thereof has occurred at room temperature for 24 hours. Then, the insoluble reactant was filtered away and the solvent was completely removed therefrom, and then a white solid was separated and purified via open column chromatography (DCM/MeOH, 99:1). The white solid was 2,5-dioxopyrrolidin-1-yl4-([1,1'-biphenyl]-4-yl)-4-oxobutanoate) (hereinafter, compound (7)) (yield: 1.65 g (48%)).

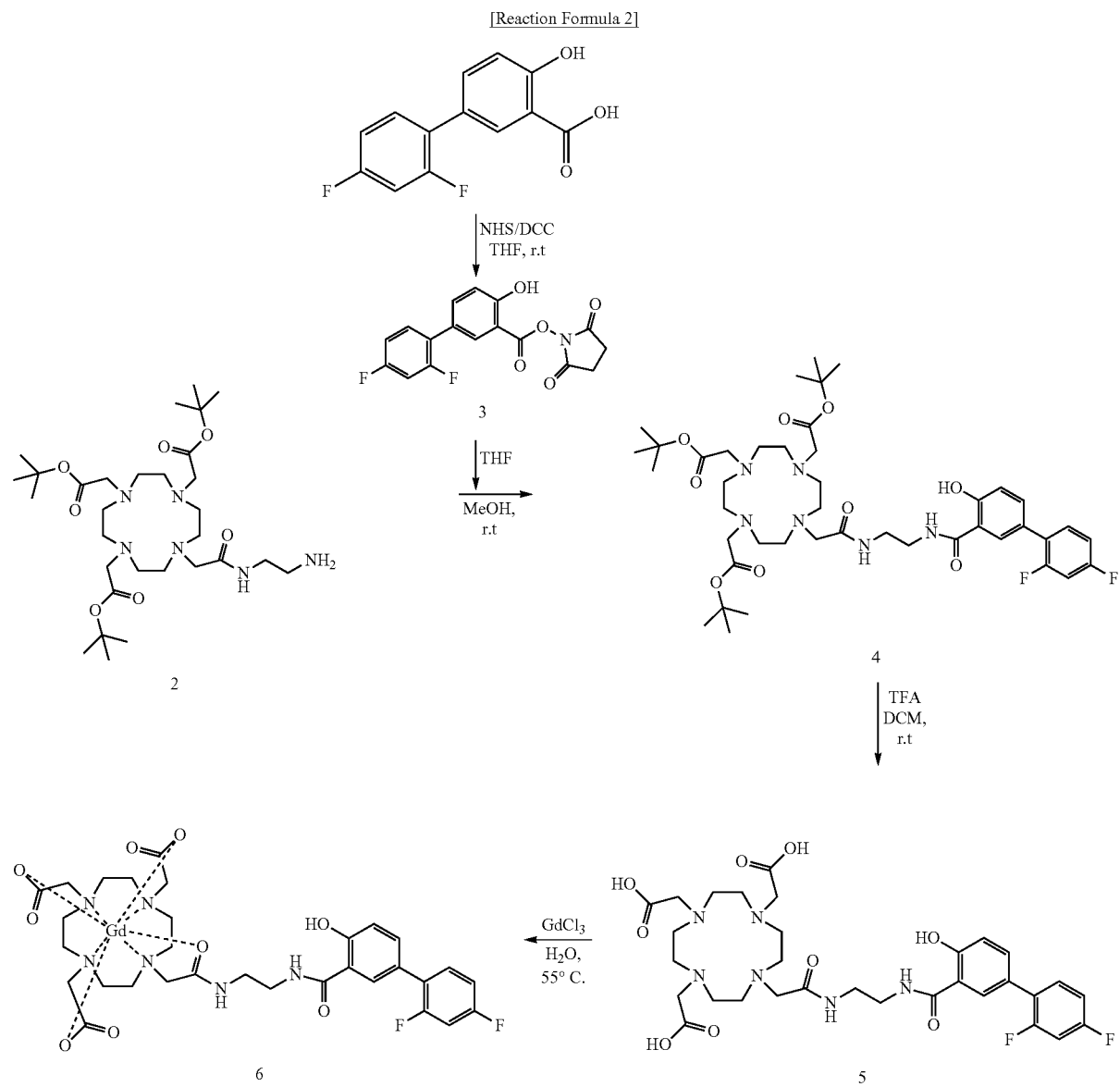

In the Reaction Formula 2, 2 refers to the compound (2), 3 refers to the compound (3), 4 refers to the compound (4), and 5 refers to the compound (5), and 6 refers to GdL (6).

Then, the compound (7) (1.95 g, 5.55 mmol) dissolved in 20 mL THF and the compound (2) (2.84 g, 4.63 mmol) dissolved in 20 mL MeOH were mixed with each other and reacted with each other at room temperature for 24 hours. Then, the solvent was completely removed therefrom, and extraction was performed under a DCM/deionized water condition. The DCM layer was dehydrated with $Na_2SO_4$ and the solvent was removed therefrom. Then, a white solid was separated and purified via open column chromatography (DCM/MeOH, 96:4). The white solid was tri-tert-butyl2,2', 2"-(10-(2-((2-(4-([1,1'-biphenyl]-4-yl)-4-oxobutanamido) ethyl)amino)-2-oxoethyl)-1,4,7,10-tetraazacyclododecane-1,4,7-triyl)triacetate) (hereinafter, compound (8)) (yield: 2.46 g (51%)).

Subsequently, the compound (8) (1.68 g, 1.98 mmol) was dissolved in DCM/TFA (1:1, 40 mL) at 0° C., and then reaction thereof has occurred at room temperature for 24 hours. The solvent of the reactant was removed therefrom, and the reaction product was dissolved in 10 mL of MeOH and precipitated in 200 mL of diethyl ether. The precipitate was filtered and was subjected to prep. HPLC, thereby to separate and obtain 2,2',2"-(10-(2-((2-(4-([1,1'-biphenyl]-4-yl)-4-oxobutanamido)ethyl)amino)-2-oxoethyl)-1,4,7,10-tetraazacyclododecane-1,4,7-triyl)triacetic acid) (hereinafter, compound (9)) as a white solid (yield: 1.56 g (94%)).

Then, the compound (9) (0.25 g, 0.368 mmol) was dissolved in deionized water and pH of the solution was adjusted to 3 using 1 M NaOH to form a first solution. Then, $GdCl_3 \cdot 6H_2O$ (0.15 g, 0.405 mmol) was dissolved in 1 mL of water to form a solution which in turn was gradually added to the first solution. Then, pH of the mixed solution was adjusted to 7 using 1 M NaOH and then reaction thereof has occurred at 55° C. for 18 hours. Then, the solvent was removed therefrom. Then, a white solid was separated and purified using prep. HPLC. The white solid as obtained was a compound (hereinafter, GdL (10)) according to Example 2 of the present disclosure (yield: 0.2 g (65%)).

A synthesis reaction of the compound according to Example 2 of the present disclosure may be expressed as a following Reaction Formula 3:

[Reaction Formula 3]

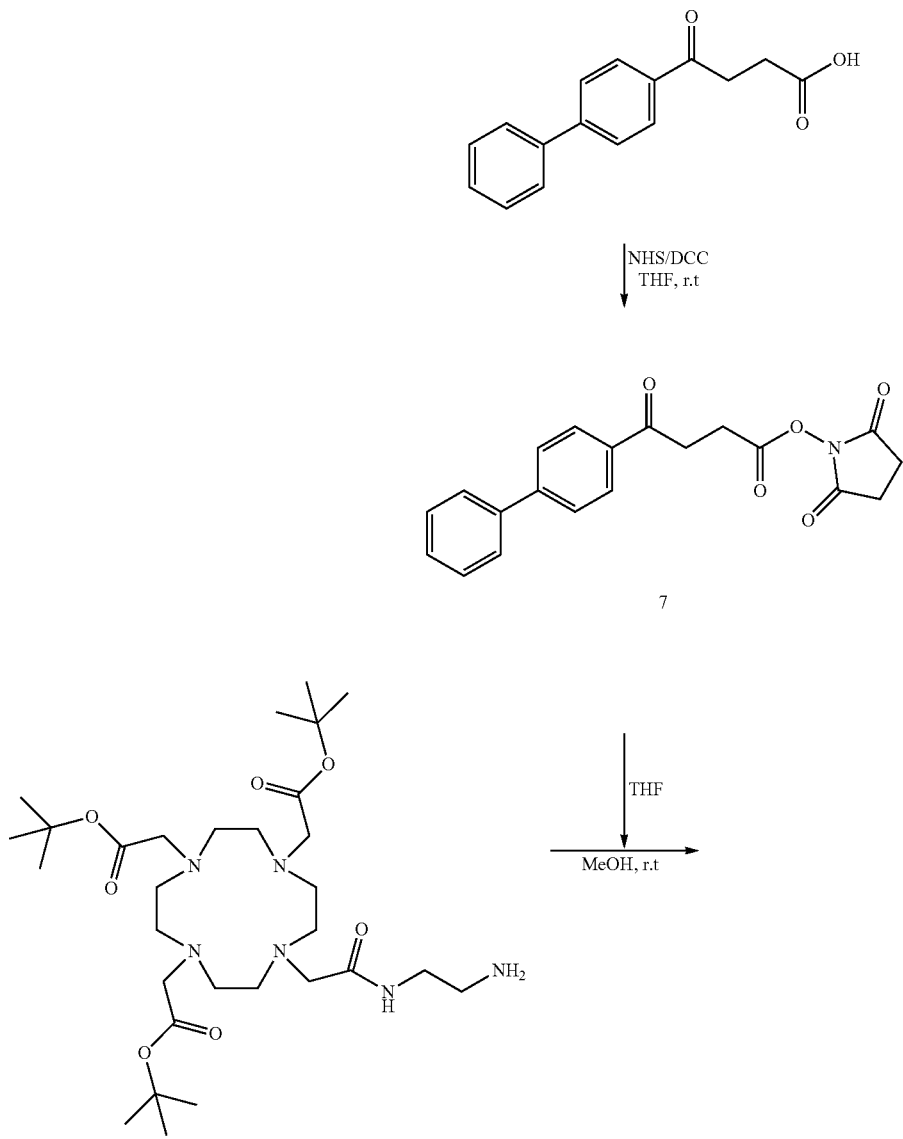

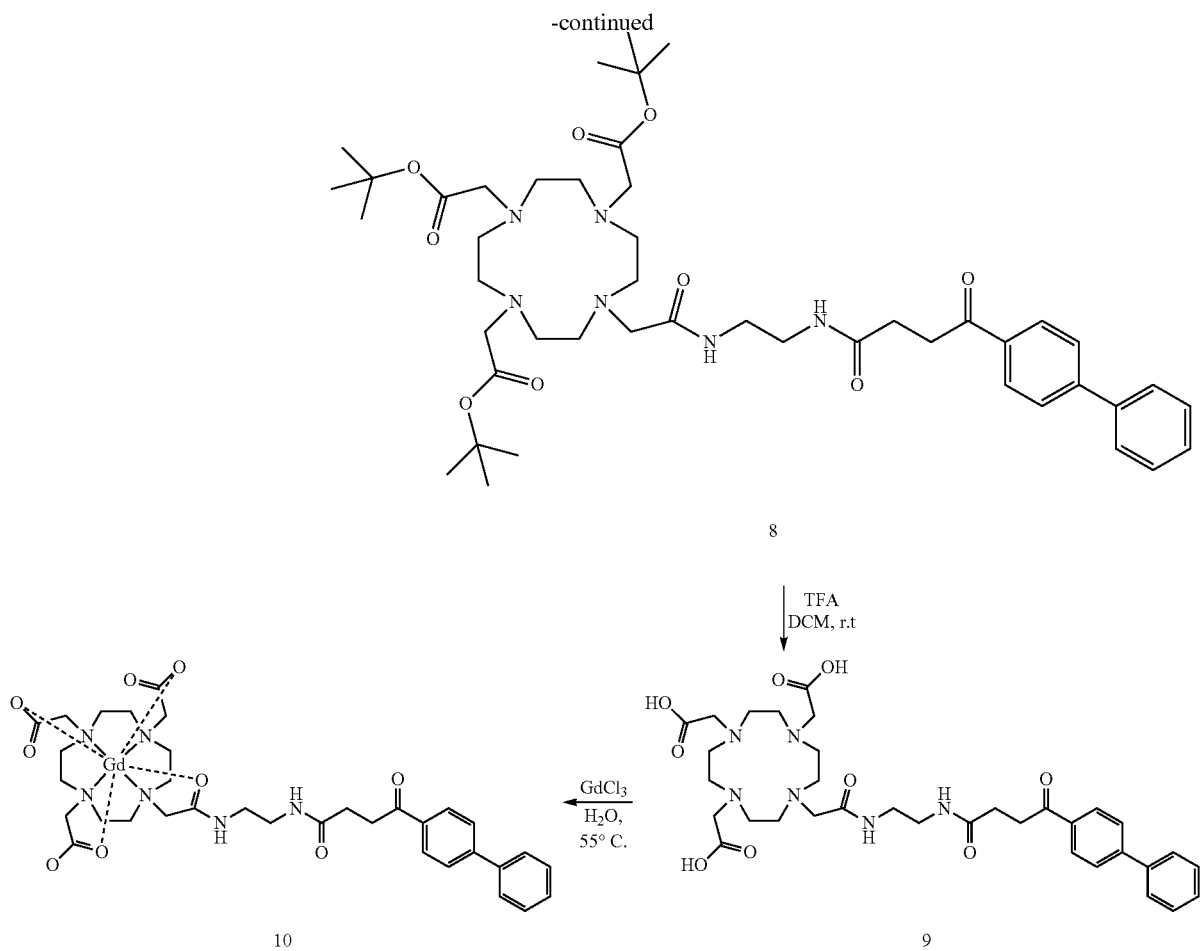

In the Reaction Formula 3, 2 represents the compound (2), 7 represents the compound (7), 8 represents the compound (8), 9 represents the compound (9), and 10 represents GdL (10).

(4) Synthesis of GdL (14) as Comparative Compound

In a Comparative Example according to the present disclosure, a comparative compound was prepared using sulindac. Specifically, sulindac (1.7 g, 4.77 mmol) was dissolved in 40 mL THF, and N-hydroxysuccinimide was added thereto, followed by stirring thereof for 30 minutes to form a reaction mixture. N,N'-dicyclohexylcarbodiimide (DCC) was dissolved in 30 mL THF to form a solution which was slowly added to the reaction mixture at 4° C., and then reaction thereof has occurred at room temperature for 24 hours. Subsequently, the insoluble reactant was filtered away therefrom and the solvent was completely removed therefrom, and then a yellow solid was separated and purified via open column chromatography (DCM/MeOH, 99:1). The yellow solid as obtained was 2,5-dioxopyrrolidin-1-yl(Z)-2-(5-fluoro-2-methyl-1-(4-(methylsulfinyl)benzylidene)-1H-inden-3-yl)acetate) (hereinafter, compound (11)) (yield: 1.17 g (51%)).

Then, the compound (11) (2.5 g, 5.5 mmol) dissolved in 20 mL THF and the compound (2) (2.83 g, 4.6 mmol) dissolved in 20 mL MeOH were mixed and reacted with each other at room temperature for 24 hours. Then, the solvent was completely removed therefrom, and extraction was performed under a DCM/deionized water condition. Then, the DCM layer was dehydrated with $Na_2SO_4$, and the solvent was removed therefrom. Then, a yellow solid was separated and purified via open column chromatography (DCM/MeOH, 96:4). The yellow solid as obtained was tri-tert-butyl2,2',2"-(10-(2-((2-(2-(5-fluoro-2-methyl-1-(4-(methylsulfinyl)benzylidene))-1H-inden-3-yl)acetamido)ethyl)amino)-2-oxoethyl)-1,4,7,10-tetraazacyclododecane-1,4,7-triyl)(Z)-triacetate) (hereinafter, compound (12)) (yield: 2.46 g (51%)).

Subsequently, the compound (12) (2.5 g, 2.95 mmol) was dissolved in DCM/TFA (1:1, 40 mL) at 0° C., and then reaction thereof has occurred at room temperature for 24 hours. Then, the solvent of the reactant was removed therefrom and then the reaction product was dissolved in 10 mL of MeOH and precipitated in 200 mL of diethyl ether. Subsequently, the precipitate was filtered and was subjected to prep. HPLC to obtain a yellow solid which was Z)-2,2',2"-(10-(2-((2-(2-(5-fluoro-2-methyl-1-(4-(methylsulfinyl)benzylidene)-1H-inden-3-yl)acetamido)ethyl)amino)-2-oxoethyl)-1,4,7,10-tetraazacyclododecane-1,4,7-triyl)triacetic acid) (hereinafter, compound (13)) (yield: 0.45 g (22%)).

Then, the compound (13) (0.25 g, 0.368 mmol) was dissolved in deionized water and pH of the solution was adjusted to 3 using 1 M NaOH to form a first solution. $GdCl_3 \cdot 6H_2O$ (0.15 g, 0.405 mmol) was dissolved in 1 mL of water to form a solution which in turn was gradually added to the first solution. pH of the mixed solution was adjusted to 7 using 1 M NaOH and then reaction thereof has occurred a temperature of 55° C. for 18 hours. Then, the solvent was removed therefrom. Then, a yellow solid was separated and purified using prep. HPLC. The obtained yellow solid was a compound (hereinafter, GdL (14)) according to Comparative Example of the present disclosure (yield: 0.18 g (58%)).

A synthesis reaction of the comparative compound GdL (14) according to the present disclosure may be expressed as a following Reaction Formula 4:

Property Evaluation: Relaxivity

Relaxivity of each of GdL (6) and GdL (10) as the compounds according to the present disclosure as prepared according to Examples 1 and 2 of the present disclosure was identified.

The relaxivity refers to a numerical value of a contrast enhancement level of a contrast agent on a magnetic resonance image (MRI). Each of GdL (6) and GdL (10) accord-

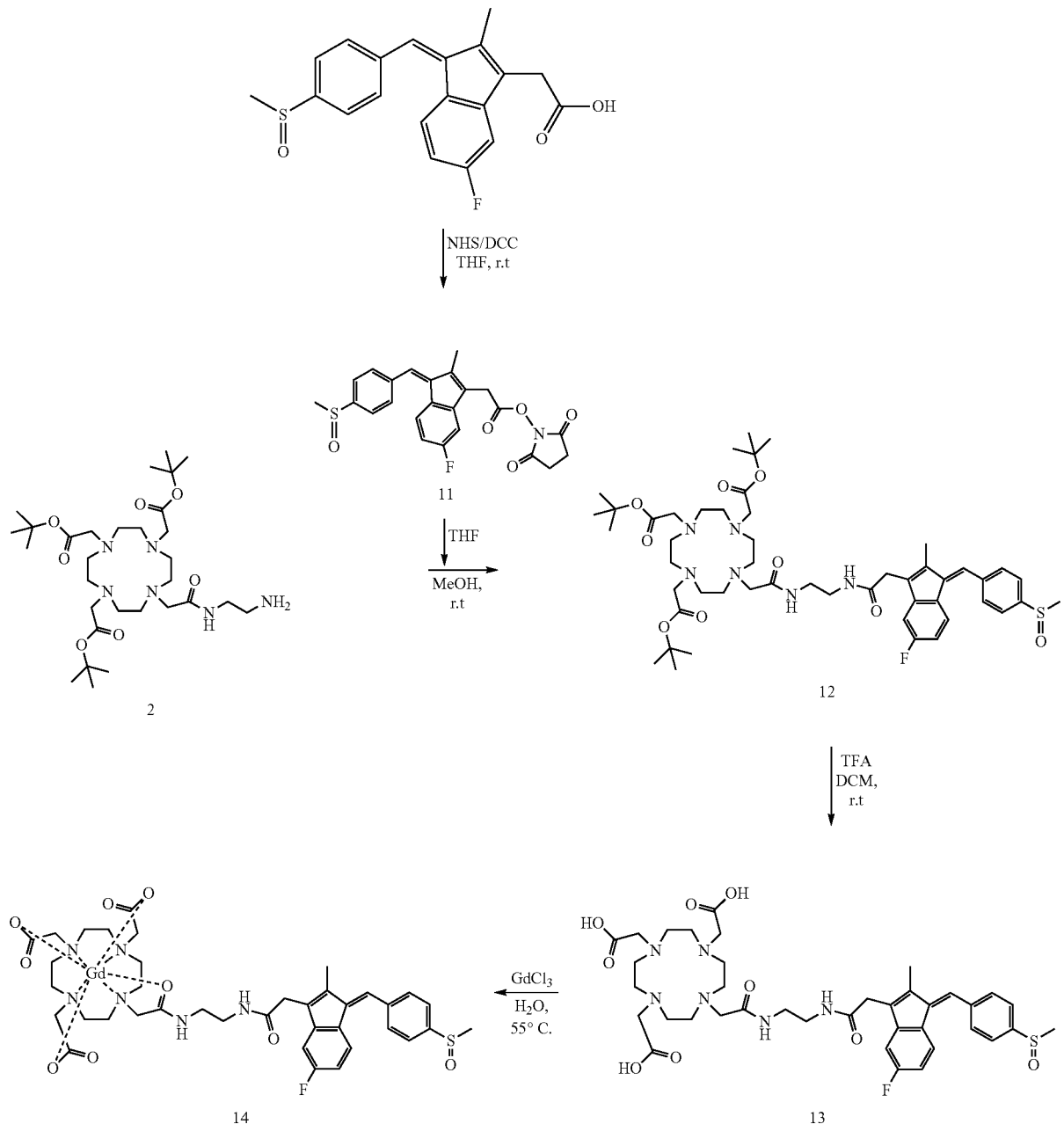

In the Reaction Formula 4, 2 represents the compound (2), 11 represents the compound (11), 12 represents the compound (12), 13 represents the compound (13), and 14 represents GdL (14).

ing to Examples 1 and 2 of the present disclosure and Gadovist® as a commercially-available contrast agent was dissolved in a PBS buffer solution (pH 7.4). The relaxivities of the three components were measured at room temperature (25° C.) and 1.5 T and then compared to each other. Then, whether the contrast enhancement effect of GdL (6) and GdL (10) according to the present disclosure was effective was evaluated based on a comparison result. The results are shown in Table 1.

TABLE 1

|  | $r_1[mM^{-1}s^{-1}]$ | $r_2[mM^{-1}s^{-1}]$ |
| --- | --- | --- |
| GdL(6) | 4.54 ± 0.20 | 4.63 ± 0.30 |
| GdL(10) | 4.95 ± 0.19 | 4.69 ± 0.17 |
| Gadovist ® | 4.12 ± 0.15 | 4.55 ± 0.18 |

Table 1 shows relaxivity results of GdL(6) and GdL(10) according to Examples 1 and 2 of the present disclosure and the commercially-available contrast agent Gadovist®.

Referring to the Table 1, relaxivity of GdL(6) according to Example 1 of the present disclosure has $r_1$=4.54±0.20, and $r_2$=4.63±0.30. Relaxivity of GdL(10) according to Example 2 of the present disclosure has $r_1$=4.95±0.19, and $r_2$=4.69±0.17. Relaxivity of Gadovist® as a control has $r_1$=4.12±0.15 and $r_2$=4.55±0.18. This indicates that the compounds according to the present disclosure, that is, GdL(6) and GdL(10) exhibit higher relaxivity than that of Gadovist® as a commercially-available contrast agent. Thus, it may be evaluated that the compounds according to the present disclosure have high relaxivity such that the compound may be used as a contrast agent for obtaining an in vivo magnetic resonance image. That is, it may be identified that the compound according to the present disclosure may be used as an excellent contrast agent.

Property Evaluation: Kinematic Stability

Further, the kinematic stability of each of GdL (6) and GdL (10) as the compounds according to Examples 1 and 2 of the present disclosure was identified. The kinematic stability of GdL (6) and GdL (10) may be identified based on change in relaxivity over time. Specifically, zinc chloride ($ZnCl_2$) was added to each of a solution in which each of GdL (6) and GdL (10) was dissolved, and then a transmetallation reaction between gadolinium and zinc ions was induced, and relaxivity thereof was measured. In this connection, it may be evaluated that as the change in relaxivity after zinc ion addition is greater, the compound is more unstable. In addition, the kinematic stability of each of four commercially-available contrast agents (Dotarem®, Multihance®, Gadovist® and Primovist®) along with GdL (6) and GdL (10) according to the present disclosure was evaluated. The kinematic stability of each of four commercially-available contrast agents (Dotarem®, Multihance®, Gadovist® and Primovist®) was compared with that of each of GdL (6) and GdL (10) according to the present disclosure. The results are shown in FIG. 1.

FIG. 1 is a diagram to describe the kinematic stability of the compound according to the present disclosure.

Referring to FIG. 1, it may be identified that the relaxivity change of each of GdL (6) and GdL (10) according to Examples 1 and 2 of the present disclosure has a value between the relaxivity changes of Dotarem® and Gadovist® among the four commercially-available contrast agents. In other words, it may be seen that each of GdL (6) and GdL (10) according to the present disclosure not only exhibit significantly higher change in relaxivity than that of each of Primovist® and Multihance® as commercially-available contrast agents of a linear structure with relatively low stability, but also exhibit similar high kinematic stability to that of each of Dotarem® and Gadovist® as the commercially-available contrast agents having a stable ring structure.

In other words, it may be identified that the compound according to the present disclosure exhibits excellent kinematic stability.

Property Evaluation: Inflammation Targeting Ability

The in vivo inflammation targeting ability of GdL (6) and GdL (10) according to Examples 1 and 2 of the present disclosure was identified and evaluated. Specifically, in vivo distribution and inflammation targeting function of each of GdL (6) and GdL (10) was identified and evaluated based on in vivo MRI experiments in an animal model having thigh inflammation. The in vivo distribution and inflammation targeting function of each of GdL (6) and GdL (10) was compared with those of Gadovist as a commercially-available contrast agent. The evaluation results of the in vivo distribution and inflammation targeting ability of each of GdL (6) and GdL (10) according to the present disclosure and the commercially-available contrast agent Gadovist® are shown in FIG. 2A to FIG. 2D.

FIG. 2A and FIG. 2B are diagrams to describe the evaluation result of the inflammation targeting ability of the compounds according to the present disclosure. FIG. 2C is a diagram to describe the evaluation result of the inflammation targeting ability of the commercially-available contrast agent Gadovist®.

FIG. 2D is a CNR graph to describe the inflammation targeting ability results of the compounds according to the present disclosure and the commercially-available contrast agent Gadovist®.

First, referring to FIG. 2A to FIG. 2C, Gadovist® shows a bright inflammation site immediately after injection thereof, but, thereafter, the signal enhancing effect thereof gradually decreases. To the contrary, it may be identified that each of GdL (6) and GdL (10) according to the present disclosure exhibits a steady signal enhancement effect for more than 2 hours immediately after injection thereof.

Further, referring to FIG. 2D, when the CNR graph shows the inflammation targetability of each of GdL (6) and GdL (10) according to the present disclosure and Gadovist®, the CNRs thereof immediately after injection thereof are similar to each other, but, thereafter, the difference between CNR of each of GdL (6) and GdL (10) according to the present disclosure and CNR of Gadovist® gradually increases over time. In particular, it may be identified that the difference between CNR of each of GdL (6) and GdL (10) according to the present disclosure and CNR of Gadovist® is at least 4 times when 2 hours have elapsed.

That is, as shown in FIG. 2A to FIG. 2D, it may be identified that the compounds GdL (6) and GdL (10) according to the present disclosure exhibit superior inflammation targeting ability than that of the commercially-available contrast agent.

Property Evaluation: Anti-Inflammatory Properties

Further, anti-inflammatory properties of the compounds GdL (6) and GdL (10) according to the present disclosure were identified. Anti-inflammatory properties were evaluated based on in vitro experiments. Specifically, cells were treated with lipopolysaccharide (LPS) as an inflammation-inducing substance, thereby to induce an inflammatory reaction. Then, the cells were treated with each of the three NSAIDs (diflunisal, fenbufen and sulindac), and were treated with each of the compounds GdL (6) and GdL (10) according to the present disclosure, and the comparative compound GdL (14) according to the present disclosure. Then, immunofluorescence images thereof were taken to identify COX-2 inhibitory ability thereof in the cells. The results are shown in FIG. 3.

FIG. 3 is a diagram to describe the anti-inflammatory properties of the compounds according to the present disclosure.

(A) in FIG. 3 shows a fluorescence image of the cells after LPS-treated cells are treated with each of diflunisal, fenbufen, sulindac, GdL (6), GdL (10) and GdL (14). (B) in FIG. 3 shows a graph of quantifying COX-2 expressing cells.

In FIG. 3, "Control" represents untreated cells, "LPS" indicates cells treated with LPS, and "LPS+Diflunisal", "LPS+Fenbufen", "LPS+Sulindac", "LPS+GdL (6)", "LPS+GdL (10)" and "LPS+GdL (14)" denote LPS-treated cells as further treated with diflunisal, fenbufen, sulindac, GdL (6), GdL (10) and GdL (10), respectively.

Referring to FIG. 3, it may be seen that when comparing the control (Control) and the LPS-treated cells (LPS) with each other, green fluorescence appears only in the LPS-treated cells. The green fluorescence indicates the presence of COX-2 which is induced by an inflammatory reaction in cells via treatment with LPS. COX-2 refers to a representative cytokine induced in the process of inflammation. The expression and increase of COX-2 is a measure of inflammation. That is, the green fluorescence in the cells means that inflammation occurs and COX-2 is present, and the level of inflammation may be identified based on the level of the green fluorescence.

Thus, when comparing the cell fluorescence when the LPS-treated cells are treated with diflunisal with the cell fluorescence when the LPS-treated cells are treated with GdL (6) according to the present disclosure, it may be identified that the fluorescence in treatment with only diflunisal ('LPS+Diflunisal') is slightly lower than that in cells (LPS) treated with only LPS, but there is still higher green fluorescence in treatment with only diflunisal ('LPS+Diflunisal'). The green fluorescence in the case where the LPS-treated cells are treated with GdL (6) according to the present disclosure ('LPS+GdL (6)') is significantly reduced and hardly appears in a visual manner, compared to the green fluorescence in treatment with only diflunisal ('LPS+Diflunisal'). Further, in particular, as shown in (B) in FIG. 3, it may be identified that treatment with GdL (6) according to the present disclosure objectively exhibits lower quantitative value of COX-2 positive cells than that in treatment with diflunisal. This means that when the LPS-treated cells are treated with GdL (6) according to the present disclosure, the expression of COX-2 is significantly suppressed, compared to a case when the LPS-treated cells are treated with only diflunisal. In other words, it may be identified that GdL (6) according to the present disclosure exhibits very excellent anti-inflammatory effects objectively.

In addition, when comparing the cell fluorescence when the LPS-treated cells are treated with fenbufen with the cell fluorescence when the LPS-treated cells are treated with GdL (10) according to the present disclosure, it may be identified that the green fluorescence in the case where the LPS-treated cells are treated with GdL (10) according to the present disclosure ('LPS+GdL (10)') is significantly reduced in a visual manner, compared to the green fluorescence in treatment with only fenbufen ('LPS+Fenbufen'). It may be identified that the green fluorescence hardly appears on the cells treated with GdL (10) according to the present disclosure. Thus, as shown in (B) in FIG. 3, it may be identified that treatment with GdL (10) according to the present disclosure objectively exhibits lower quantitative value of COX-2 positive cells than that in treatment with fenbufen. This means that when the LPS-treated cells are treated with GdL (10) according to the present disclosure, the expression of COX-2 is significantly suppressed, compared to a case when the LPS-treated cells are treated with only fenbufen. That is, it may be identified that GdL (10) according to the present disclosure has excellent COX-2 inhibition and anti-inflammatory effects.

Therefore, when cells having inflammatory reaction are treated with GdL (6) and GdL (10) according to the present disclosure, COX-2 expression may be more significantly inhibited, compared to a case when cells having inflammatory reaction are treated with diflunisal and fenbufen as the commercially-available anti-inflammatory agents. Accordingly, it may be identified that GdL (6) and GdL (10) according to the present disclosure have excellent anti-inflammatory properties.

Further, when LPS-treated cells were treated with sulindac ('LPS+Sulindac'), excellent COX-2 inhibition ability is achieved. When a derivative of GdL (14) is used, COX-2 inhibitory ability decreases, and, thus, the higher green fluorescence may be identified, compared to a case when sulindac is used. This means that all of the compounds containing the DO3A-based gadolinium complex ligand according to the present disclosure do not have the same anti-inflammatory properties. A more detailed description thereof will be provided later.

Further, in order to more specifically describe the selective inhibition of COX-2, western blotting was performed on the three kinds of NSAIDs (diflunisal, fenbufen, and sulindac) and the compound GdL (6) and GdL (10) according to the present disclosure and comparative compound GdL (14) according to the present disclosure in terms of inhibition of expression of several cytokines involved in inflammation expression including COX-2 expressed via the LPS treatment. The results are shown in FIG. 4.

FIG. 4 is a diagram to describe the COX-2 selective inhibition property of the compounds according to the present disclosure.

(A) in FIG. 4 shows the Western blot results after treatment with diflunisal, fenbufen, sulindac, GdL (6), GdL (10) and GdL (14) respectively, in terms of the inhibition of cytokines. (B) in FIG. 4 shows a graph that quantifies COX-2 versus β-acitin.

Referring to FIG. 4, when identifying a COX-2 band in (A) in FIG. 4, it may be identified that treatment with diflunisal and fenbufen do not achieve COX-2 inhibition effect. However, it may be identified that GdL (6) and GdL (10) according to the present disclosure greatly inhibits the COX-2 expression. In other words, it may be identified that treatment with the compounds GdL (6) and GdL (10) according to the present disclosure achieves very excellent COX-2 selective inhibition property, and thus exhibits very excellent anti-inflammatory properties, compared to both of treatment with only LPS and treatment with each of the conventional anti-inflammatory drugs after the LPS treatment.

Further, it may be identified based on FIG. 3 that sulindac has COX-2 inhibition ability, while Comparative Example GdL (14) has reduced inhibition effect of COX-2. This is consistent with the immunofluorescence result as described with reference to the FIG. 3. That is, it may be identified based on the immunofluorescence results and Western blot results that unlike the comparative compound GdL (14), the GdL (6) and GdL (10) according to the present disclosure exhibit excellent selective inhibition properties of COX-2. This indicates that when conjugating COX-1 and COX-2 non-selective diflunisal and fenbufen with DO3A based gadolinium complex ligand according to the present disclosure, a novel anti-inflammatory substance that may be used as a contrast agent and exhibit very good COX-2 inhibition properties and improved anti-inflammatory properties at a level similar to that of sulindac known as a COX-2 selective inhibitor may be provided based on a COX-2 non-selective anti-inflammatory substance.

That is, it may be identified based on the above findings that the compound according to the present disclosure exhibits excellent relaxivity, and exhibits strong contrast enhancement at the inflammation site and long-term targetability to the inflammation site in the inflammatory disease animal model experiments, and exhibits excellent stability in the body in the kinematic stability test. Therefore, it may be identified that the compound according to the present disclosure has excellent relaxivity and kinematic stability, so that the compound may be used as a contrast agent, but may target the inflammation site and has anti-inflammatory properties via excellent COX-2 selective inhibition at the inflammation site. Furthermore, the compound according to the present disclosure has anti-inflammatory properties superior to the conventional anti-inflammatory substances, and, in particular, may selectively inhibit the expression of COX-2 induced by the inflammatory reaction, and thus may minimize the problems/side effects such as gastrointestinal diseases due to the non-selective inhibition of COX-1 and COX-2 which the conventional anti-inflammatory agents have, and may effectively treat the inflammatory disease via the selective inhibition of COX-2 relative to COX-1.

Therefore, it may be identified that the compound according to the present disclosure has targetability toward inflammation, targets and diagnoses the inflammation site, and, at the same time, has excellent COX-2 selective inhibition ability, and thus may be used as the COX-2 selective inhibitor enabling the inflammation treatment or the anti-inflammatory agent achieving the inflammation diagnosis and treatment at the same time. It may be identified that the anti-inflammatory agent and the COX-2 inhibitor, each containing the compound according to the present disclosure exhibit excellent activity.

Analysis of Therapeutic Efficacy in Middle Cerebral Artery Occlusion-Reperfusion (MCAO-R) Stroke Animal Model The MCAO-R stroke model was used to identify the therapeutic efficacy of GdL (14) and GdL (6) synthesized in a following example in an animal model of brain inflammation. To induce the MCAO-R stroke model, Sprague Dawley (SD) rats of 7 weeks of age were first anesthetized with isoflurane at a concentration of 2.5%. Then, a nylon filament was inserted into the rat through ECA (external carotid artery) while blocking CCA (common carotid artery) to occlude the middle cerebral artery (MCA) for 45 minutes, and then reperfusion of blood was performed. Thus, a stroke was induced. First, the expression levels of the inflammatory factor cyclooxygenase-2 at 0, 1, 3, 6, 12, 24, 48 hours after the reperfusion were measured using Western blot analysis. The cerebral infarction induced by the stroke was analyzed by cutting a whole brain isolated 24 hours after the reperfusion into a 2 mm section, and staining the section with 2% triphenyltetrazolium chloride. Western blot analysis was performed as follows. We extracted a protein in the brain tissue using a protein extraction buffer (50 mM Tris-HCl (pH 8.0), 5 mM EDTA, 150 mM NaCl, 1% NP-40, 0.1% SDS, 1 mM PMSF, and one protease inhibitor cocktail tablet (Roche, Germany)) and centrifuged (10,000×g, 15 minutes, 4° C.) the protein to obtain a protein extract. Protein concentration was quantified using a BCA protein assay kit (Pierce, Ill.). 10 μg protein sample was mixed with SDS-PAGE sample buffer (100 mM Tris-HCl, 2% SDS, 1% 2-mercaptoethanol, 2% glycerol, 0.01% bromophenol blue, pH 7.6) and the mixture was heated (at 100° C. and for 5 minutes). Thus, the protein sample was denatured. Electrophoresis thereof was performed with 10% polyacrylamide gel. Mini protean 3 Cell (Bio-Rad, CA) was used for electrophoresis. The protein separated on a gel was transferred to a nitrocellulose membrane (Whatman, Germany), and the protein transfer and the amount of spotted protein were identified using Ponceau S staining. Then, the nitrocellulose membrane was blocked with a blocking buffer (10 mM Tris-HCl, pH 7.5, 150 mM NaCl, 0.1% Tween 20, 3% nonfat dry milk) and the sample therein was cultured together with a primary antibody (dilution factor 1:1000; Cell Signaling Technology, Inc., MA). In this connection, the primary antibody was an antibody (Cell Signaling Technology, Inc., MA) that specifically binds to the inflammatory factor cyclooxygenase 2 having increased expression level in the brain inflammation and to a house keeping protein beta-actin for standardization of the amount of protein. The membrane reacted with the primary antibody was washed three times for 10 minutes with a blocking buffer, and then the sample therein was cultured together with a secondary antibody (1:2000) for 1 hour. Thereafter, after washing the membrane three times with a blocking buffer for 10 minutes, the membrane was developed with SuperSignal West Femto Maximum Sensitivity Substrate (Pierce, IL). The fluorescence signal was detected using a LAS-3000 emission image analyzer (Fuji Photo Film Co., Japan). The band density was measured using Multi Gauge software version 3.0 (Fuji Photo Film Co.).

FIG. 5A shows an animal test result for the acute cerebral stroke or vascular dementia among the brain inflammatory diseases in which a level of the brain inflammatory factor cyclooxygenase 2 (COX-2) induced by the reperfusion after the ischemic stroke increases. The level starts to increase at 3 hours since the reperfusion after the stroke and reaches the highest value at 24 hours since the reperfusion.

FIG. 5B shows the experimental result of cerebral infarction as caused by ischemic stroke. It is identified based on the result that sulindac and GdL (14) inhibit the cerebral infarction site in the similar level to each other and diflunisal and GdL (6) significantly inhibit the cerebral infarction. GdL(6) among them exhibits the strongest cerebral infarction treatment effect.

FIG. 5C shows the result of identifying, via the Western blot technique, the protein amount of COX-2 as an inflammatory factor as expressed in tissues at the cerebral infarction site caused by the ischemic stroke. It is identified based on the result that sulindan and GdL(14) have similar levels of inhibition efficacy as in the therapeutic efficacy of the cerebral infarction, and diflunisal and GdL(6) also exhibit inhibition of COX-2 activity. As in the cerebral infarction result, GdL(6) exhibits the strongest inhibitory effect on the inflammatory factor.

Property Evaluation: Cell Viability Experiment in Brain Cerebral Cortex Microglia (SIM-A9)

In order to evaluate the cell viability of GdL (14) and GdL (6) synthesized in the Examples, an experiment using CCK- 8-kit (cell counting kit-8) was conducted. When using the cell counting kit-8 (CCK-8), analysis was performed using highly water-soluble tetrazolium salt-SST-8, and [2-(2-methoxy-4-nitrophenyl)-3-(4-nitrophenyl)(2,4-disulfophenyl)-2H-tetrazolium, monosodium salt] produces a water-soluble formazan orange dye when being reduced in the presence of an electron mediator. The amount of the formazan dye produced by the dehydrogenase in cells is directly proportional to the number of living cells. In this experiment, microglia SIM-A9 (ATCC®CRL-3265™) of brain cerebral cortex derived from mouse was used. Cells maintained in a complete growth medium containing 5% heat-inactivated horse serum and 10% heat-inactivated FBS in DMEM/F-12 medium were suspended in 200 µl volume thereof at a density of $1.5 \times 10^4$ cells and then the medium was plated into each well of a 96 well plate. The plate was attached to 37° C., 5% $CO_2$ incubator and was maintained for more than 14 hours to be stabilized. The next day, we removed the medium from the well. Then, 100 µl of DMEM/F-12 serum free medium containing each of various concentrations (0(control), 5, 10, 30, 50, 100, 200 µM) of each of DIF, Gd-DIF, FEN, Gd-FEN, SUL, and Gd-SUL was added to each well and the cells were cultured. On 22 hours after the incubation initiation, 10 µl of the CCK-8 solution was added to each well and the cells were further incubated for 2 hours. The plate on which the culture of the cells was completed was measured in terms of absorbance at 450 nm using a microplate reader. Cell viability calculation is as follows.

Cell Viability Calculation:

A: absorbance value measured in control well
B: absorbance value measured in well containing drug $$\text{Cell viability (\%)} = \frac{B}{A} \times 100 \ (\%)$$

The calculated values were graphed using the GraphPad Prism application. The statistical significance of the numerical values was identified via One-way ANOVA with Dunnett's multiple comparison test. This test indicates significance of * $p<0.05$  $p<0.01$,* $p<0.001$ vs. control.

FIG. 6 shows based on a result of the cell viability test in the brain cerebral cortex microglia that both of GdL(6) and GdL(14) substances developed in the brain cerebral cortex microglia allow superior cell viability at high concentrations thereof, compared to the conventional substances diflunisal and sulindac, and thus have reduced toxicity than those of the conventional drugs.

Property evaluation: MRI diagnostic ability of acute stroke or vascular dementia among brain inflammatory diseases To evaluate the MRI diagnostic ability in the stroke model of GdL (14) and GdL (6) synthesized in the Examples, diagnostic ability was evaluated using the same animal model used for evaluation of the treatment efficacy. In the same animal model, the drug was injected through the tail vein 6 hours after reperfusion, and images were acquired every hour until 3 hours after the drug administration. The experiment was carried out on an animal MRI of Bruker 4.7 T and a 4-channel array coil was used. The images were adapted to the same window level in the imageJ program and were compared with each other. All of a T2 weighted image, a diffusion tensor image (DTI), and a T1 weighted image which are used for diagnostic purposes in actual clinical practice for stroke patients were acquired. In the early stage of stroke, precise diagnosis may not be performed based on the T2 weighted images and the ischemia site may be predicted based on the diffusion tensor image. However, since an image such as DTI is an image calculated via image processing, there is a problem in that accuracy and reliability in predicting an accurate ischemia site and cerebral infarction size are inferior based on the DTI image. Therefore, the development of an MRI contrast agent that accurately targets the inflammatory site generated at the cerebral infarction site and accurately diagnoses the cerebral infarction site has great significance.

FIG. 7 shows that both GdL(6) and GdL(14) enhance the ischemia site signal in the stroke animal model. In particular, GdL(6) starts to exhibit a strong signal enhancement effect on 1 hour after the drug injection, and targets only the cerebral infarction site on 3 hours after the drug injection such that the signal strongly increases. GdL(14) starts to exhibit a strong signal enhancing effect on the ischemia site on 2 hours after the drug injection and maintains the enhanced signal on up to 3 hours after the drug injection.

Property Evaluation: Targetability Evaluation Via Binding Affinity Experiment with COX-2 Protein A UV-spectrophotometer experiment was conducted to evaluate the direct binding affinity of GdL (10), GdL (14) and GdL (6) as synthesized in the Examples with the COX-2 protein. After measuring the intrinsic UV spectrum intensity of the developed substances, COX-2 protein was added thereto at an uniform content to measure the concentration thereof until the spectral intensity decreases and then further decreases to a saturation state. The binding affinity constant was obtained as a result of calculation using the obtained concentration and spectral intensity values. Further, fenbufen, difulunisal, and sulindac were used as comparative substances. A starting concentration of each of diflunisal, GdL(6), GdL(10), and GdL(14) was 10 M, and a starting concentration of each of fenbufen and sulindac was 5 µM. Regarding the concentration of the added COX-2, 20 µl of a solution obtained by adding 100 µl of pH7.5 Tris buffer to 9 µl of 3 M COX-2 solution was added to each of fenbufen, diflunisal, GdL(6), and GdL(10). The spectrum was measured each time 20 µl of the solution was added thereto. 20 µl of a solution obtained by adding 100 µl of a pH7.5 Tris buffer solution to 6 µl of a 3 M COX-2 solution was added to each of GdL(14) and sulindac. The spectrum was measured each time 20 µl of the solution was added thereto. An equation for calculating the binding affinity constant Ka using the measured values is as follows.

$$1/(A_f - A_{obs}) = 1/(A_f - A_{fc}) + 1/K_a(A_f - A_{fc})[L]$$

$A_f$: absorbance of compound itself
$A_{obs}$: absorbance at each addition of COX-2
$A_{fc}$: absorbance at saturated state after protein addition
[L]: Concentration of Compound FIG. 8 shows that all of the three developed substances GdL(6), GdL(10), and GdL(14) have a COX-2 target affinity that is 1.3 times higher than those of the comparative substances diflunisal, fenbufen, and sulindac, respectively and thus the inhibition ability due to the increase in the targetability toward the COX-2 is consistent with the above results.

The present disclosure has been described above with reference to the preferred embodiment of the present disclosure. However, it will be appreciated that skilled artisans in the technical field may have various modifications and alternatives of the embodiment of the present disclosure within the scope not departing from the spirit and scope of the present disclosure as described in the following claims.

What is claimed is:

1. A method for treating brain inflammation, the method comprising administering to a patient with brain inflammation a therapeutically effective amount of a composition comprising a compound having a structure represented by a following Chemical Formula 2, 3, or 4:

[Chemical Formula 2]

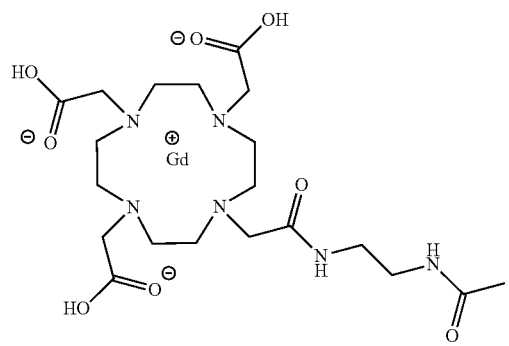

,

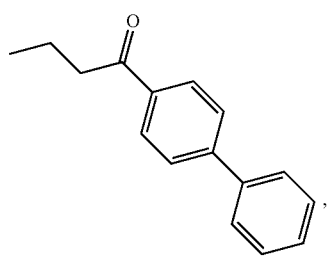

[Chemical Formula 3]

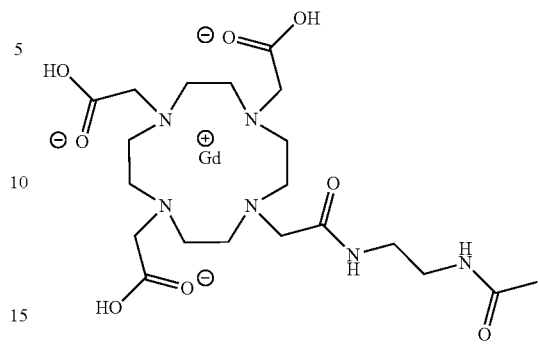

F, or

[Chemical Formula 4]

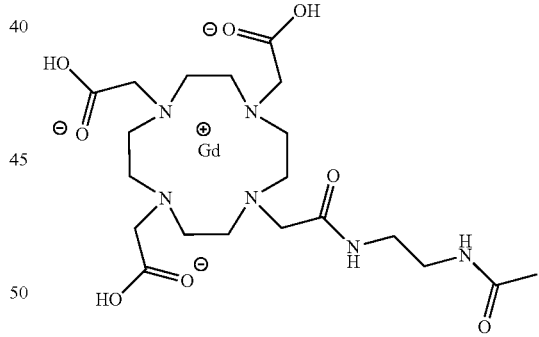

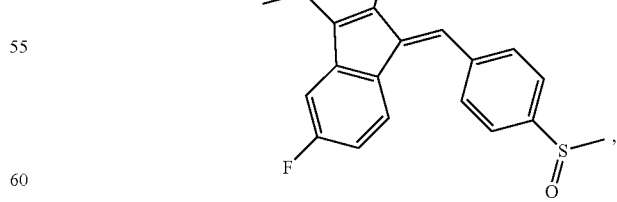

, to treat the brain inflammation in the subject, wherein the compound treats the brain inflammation in the subject.

2. The method of claim 1, wherein the compound is represented by Chemical Formula 2:

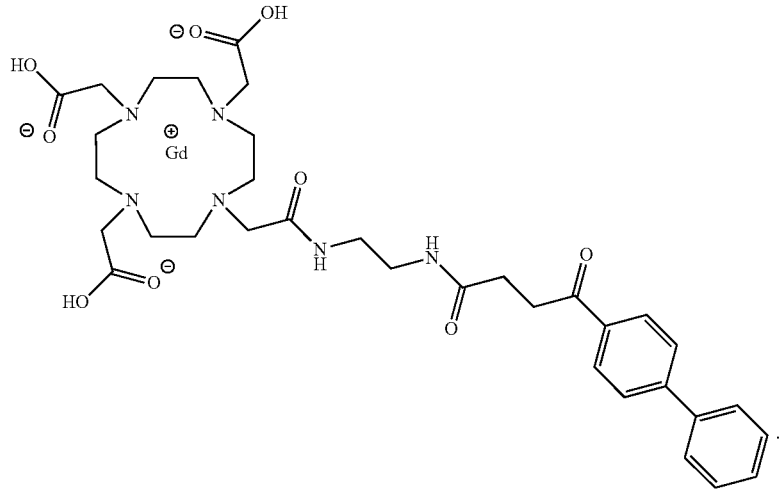
3. The method of claim 1, wherein the compound is represented by Chemical Formula 3:
[Chemical Formula 3]
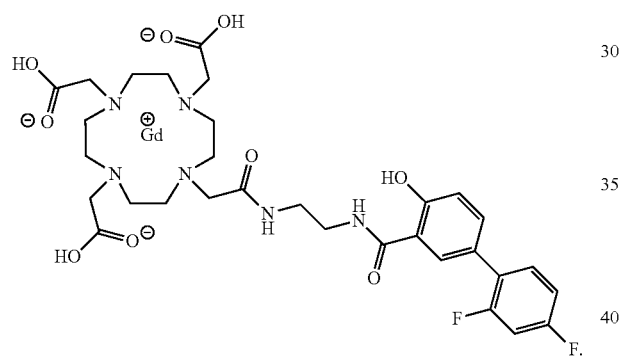
4. The method of claim 1, wherein the compound is represented by Chemical Formula 4:
[Chemical Formula 4]
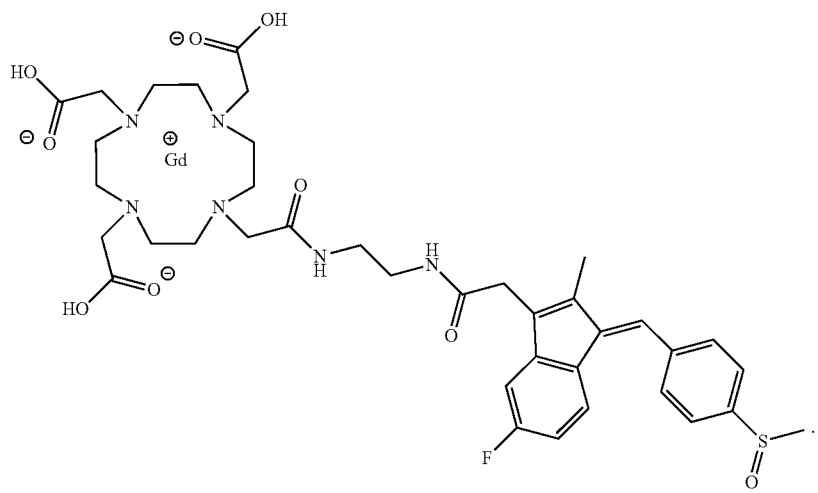

5. The method of claim 1, wherein the compound selectively inhibits cyclooxygenase-2 (COX-2) at the inflammation site.

6. A method for treating brain inflammation, the method comprising administering to a patient with brain inflammation a therapeutically effective amount of a composition comprising a compound having a structure represented by a following compound having a structure represented by a following Chemical Formula 1:

[Chemical Formula 1]

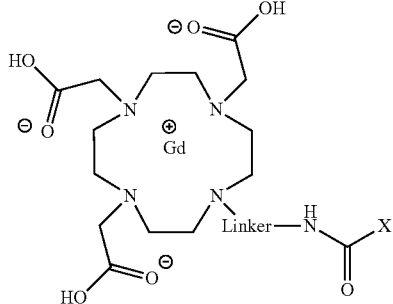

wherein in the Chemical Formula 1, the linker represents
*—$(CH_2)_x$-A-$(CH_2)_y$—*, wherein each of x and y independently represents an integer from 0 to 5, wherein A represents *—COO—*, *—CO—*, *—CONH—* or *—O—*,, wherein X represents:

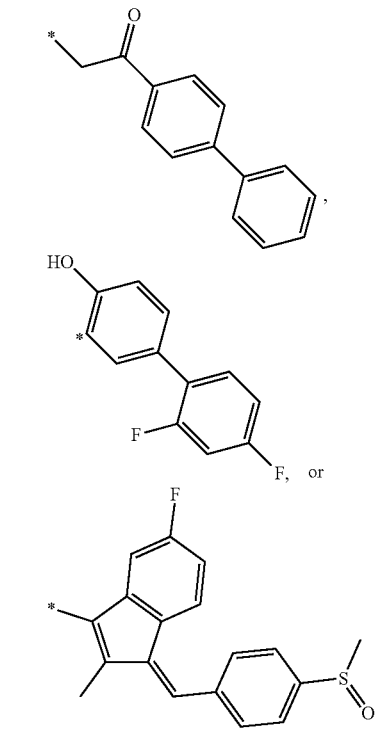

to treat the brain inflammation in the subject, wherein the compound treats the brain inflammation in the subject.

* * * * *